US008896829B2

(12) United States Patent
Furusho

(10) Patent No.: US 8,896,829 B2
(45) Date of Patent: Nov. 25, 2014

(54) METAL PARTICLES FOR SURFACE-ENHANCED RAMAN SCATTERING AND MOLECULAR SENSING

(75) Inventor: Hitoshi Furusho, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 13/704,427

(22) PCT Filed: Jun. 14, 2011

(86) PCT No.: PCT/JP2011/063589
§ 371 (c)(1),
(2), (4) Date: Dec. 14, 2012

(87) PCT Pub. No.: WO2011/158829
PCT Pub. Date: Dec. 22, 2011

(65) Prior Publication Data
US 2013/0141719 A1 Jun. 6, 2013

(30) Foreign Application Priority Data

Jun. 15, 2010 (JP) ................. 2010-136137

(51) Int. Cl.
G01J 3/44 (2006.01)
C07H 23/00 (2006.01)
G01N 21/65 (2006.01)
B22F 1/00 (2006.01)
C07H 1/00 (2006.01)

(52) U.S. Cl.
CPC .............. *C07H 23/00* (2013.01); *G01N 21/658* (2013.01); *B22F 1/0062* (2013.01); *B22F 1/0096* (2013.01); *C07H 1/00* (2013.01); *B22F 2999/00* (2013.01)
USPC .......................................... 356/301; 356/300

(58) Field of Classification Search
CPC .. B22F 2999/00; B22F 1/0062; B22F 1/0096; B22F 1/0018; B22F 2304/054; C07H 23/00; G01N 21/658
USPC ................................................ 356/300–303
See application file for complete search history.

(56) References Cited

U.S. PATENT DOCUMENTS

| 6,972,173 | B2 | 12/2005 | Su et al. |
| 2005/0147963 | A1 | 7/2005 | Su et al. |
| 2006/0040286 | A1 | 2/2006 | Mirkin et al. |

FOREIGN PATENT DOCUMENTS

| JP | A-2005-519622 | 7/2005 |
| JP | A-2005-233637 | 9/2005 |

(Continued)

OTHER PUBLICATIONS

Feldheim, "Assembly of Metal Nanoparticle Arrays Using Molecular Bridges," The Electrochemical Society Interface, pp. 22-25, Fall 2001.

(Continued)

*Primary Examiner* — Tri T Ton
(74) *Attorney, Agent, or Firm* — Oliff PLC

(57) ABSTRACT

A metal nanoparticle material for molecular sensing, that includes a metal nanoparticle aggregate including three to ten metal nanoparticles connected to each other through an organic molecule so that adjacent metal nanoparticles are bonded and spaced apart a predetermined distance, the aggregate containing a Raman active molecule within a field applied to the aggregate, wherein the metal nanoparticle material emits enhanced Raman scattering light from the Raman active molecule in an enhanced electric field; a method for producing the metal nanoparticle material for molecular sensing; and a molecular sensing method using the metal nanoparticle material for molecular sensing.

7 Claims, 11 Drawing Sheets

(56) References Cited

FOREIGN PATENT DOCUMENTS

| JP | A-2007-514169 | 5/2007 |
|---|---|---|
| JP | A-2007-537450 | 12/2007 |
| JP | A-2008-184671 | 8/2008 |
| JP | A-2008-224274 | 9/2008 |
| JP | A-2009-061580 | 3/2009 |

OTHER PUBLICATIONS

Lim et al., "Nanogap-Engineerable Raman-Active Nanodumbbells for Single-Molecule Detection," Nature Materials, vol. 9, pp. 60-67, Jan. 2010.

Hudson et al., "Bioanalytical Applications of SERS (Surface-Enhanced Raman Spectroscopy)," Anal Bioanal Chem, vol. 394, pp. 679-686, 2009.

Jan. 8, 2013 International Preliminary Report on Patentability and Written Opinion issued in International Application No. PCT/JP2011/063589.

Odom et al., "How Gold Nanoparticles Have Stayed in the Light: The 3M's Principle," American Chemical Society, vol. 2, No. 4, pp. 612-616, 2008.

Shah et al., "Lactate and Sequential Lactate-Glucose Sensing Using Surface-Enhanced Raman Spectroscopy," Anal. Chem., vol. 79, pp. 6927-6932, 2007.

Lyandres et al., "Real-Time Glucose Sensing by Surface-Enhanced Raman Spectroscopy in Bovine Plasma Facilitated by a Mixed Decanethiol/Mercaptohexanol Partition Layer," Anal. Chem., vol. 77, pp. 6134-6139, 2005.

Holzer et al., "Resonance Raman Effect and Resonance Fluorescence in Halogen Gases," The Journal of Chemical Physics, vol. 52, No. 1, pp. 399-407, Jan. 1, 1970.

Jeanmaire et al., "Surface Raman Spectroelectrochemistry," J. Electroanal. Chem., vol. 84, pp. 1-20, 1977.

Kwart et al., "Anomalously Intense Raman Spectra of Pyridine at a Silver Electrode," Journal of American Chemical Society, vol. 99, No. 15, pp. 5215-5217, Jul. 20, 1977.

Merican et al., "Self-Assembly and Encoding of Polymer-Stabilized Gold Nanoparticles with Surface-Enhanced Raman Reporter Molecules," Langmuir, vol. 23, pp. 10539-10545, 2007.

Kneipp et al., "One- and Two-Photon Excited Optical pH Probing for Cells Using Surface-Enhanced Raman and Hyper-Raman Nanosensors," Nano Lett., vol. 7, No. 9, pp. 2819-2823, 2007.

Suzuki et al., "Controlling the Number and Positions of Oligonucleotides on Gold Nanoparticle Surfaces," J. Am. Chem. Soc., vol. 131, pp. 7518-7519, 2009.

FIG. 21
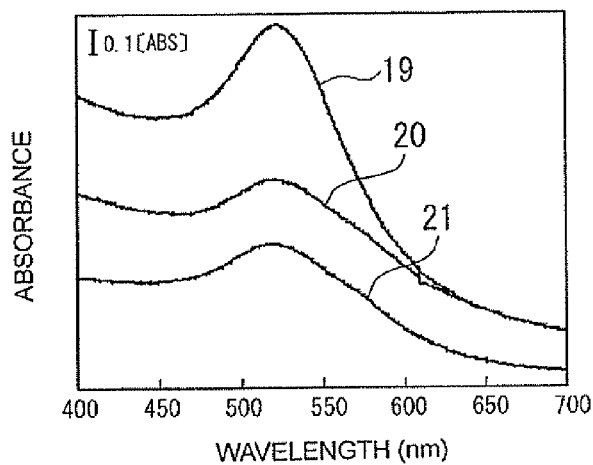
FIG. 22
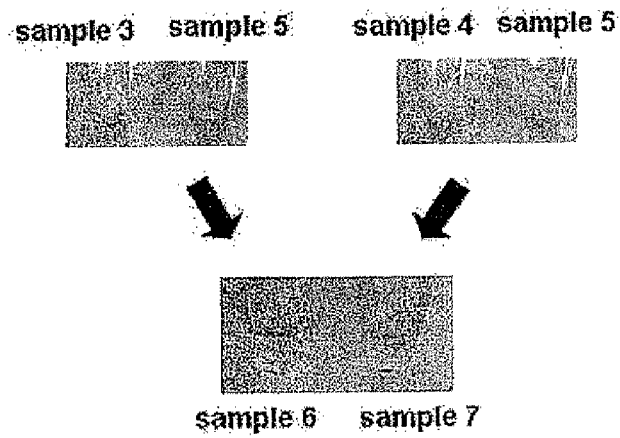
FIG. 23]
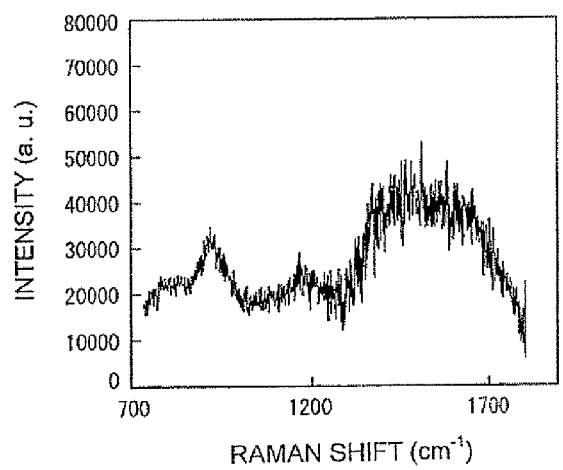

FIG. 26
PHOSPHORIC ACID
DERIVED FROM DNA OF
CANCER CELL (a549)
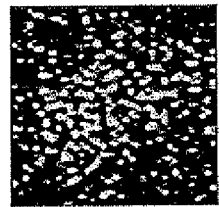
MAPPING OF SAMPLE 6
RECOGNITION PART
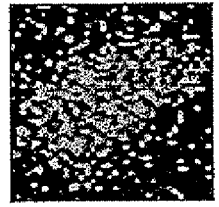
MICROGRAPH OF
CANCER CELL (a549)

METAL PARTICLES FOR SURFACE-ENHANCED RAMAN SCATTERING AND MOLECULAR SENSING

TECHNICAL FIELD

The present invention relates to a metal nanoparticle material for molecular sensing that is used for surface-enhanced Raman scattering to which a surface plasmon phenomenon is applied and a method for producing the metal nanoparticle material.

Specifically, the present invention relates to a metal nanoparticle material for molecular sensing including a metal nanoparticle aggregate containing metal nanoparticles that have surface plasmon absorption in a visible light region and that are connected to each other through organic molecules such as DNA, thereby being spaced apart a predetermined distance from each other.

BACKGROUND ART

Surface-enhanced Raman scattering (SERS) is a characteristic feature that is specifically observed in organic molecules adsorbed onto the surface of metal.

Specifically, SERS is a phenomenon in which metal particles come close to each other to generate a resonance effect on the surface of the metal particles, thereby inducing local surface plasmon, and then the local surface plasmon induces an enhanced electric field, which enhances Raman scattering from Raman active molecules (organic pigment molecules such as rhodamine 6G) adsorbed to the metal particles in the enhanced electric field.

One of the reasons why SERS draws attention is that a vibration spectrum can be obtained even from a single molecule or a single particle. This enables the detection of a trace amount of a chemical substance for biomolecular recognition, for example, and various studies have been actively carried out (Non-Patent Documents 1, 2, and 3).

Raman scattering is a physical phenomenon absolutely unsuitable for such trace detection originally due to some of its characteristics. The reason for this is considered as below.

Raman scattering is caused by a collision of a molecule to be measured with a photon emitted from laser light. For example, the number of photons emitted from an argon laser of a wavelength of 488 nm can be estimated to be about $2.5 \times 10^{18}$ per second under an output power of 1 W. Among them, the number of photons coming into collision is only about $10^{13}$ to $10^{15}$, whereas most of the photons pass through without colliding with molecules. Such a slight number of photons come into collision in two collision modes of elastic collision and inelastic collision. In elastic collision, energy is not transferred between molecules and photons and scattering caused in this collision mode is called "Rayleigh scattering." In Rayleigh scattering, energy is not transferred between photons and molecules, and hence the frequency of scattering light is accordingly the same as the wavelength of incident light. Most of the collisions between molecules and photons, which will occur at a low frequency as described above, are elastic scattering, and the scattering light is therefore largely Rayleigh scattering.

In inelastic scattering, on the contrary to elastic scattering, a photon comes into collision with a molecule and transfers its energy to the molecule. On this account, the frequency of the scattering light differs from the frequency of the incident light in contrast to Rayleigh scattering. This scattering is called Raman scattering. In particular, when Raman scattering light has a larger frequency than that of incident light (when a photon obtains energy from a molecule), such scattering is called anti-Stokes Raman scattering. When a photon conversely gives energy to a molecule, such scattering is called Stokes Raman scattering. The number of photons causing such inelastic collision is about $10^{-7}$ of the total number of photons coming into collision. As described above, with respect to the number of incident photons, the number of photons coming into inelastic collision to cause Raman scattering is very small. This leads to low detection sensitivity. This is why Raman scattering was rarely used for analysis means.

In the early 1970s, however, a large number of studies on resonance Raman, for example, the measurement of a resonance Raman scattering spectrum of gaseous halogen molecules by W. Holzer et al. (Non-Patent Document 4), were started to be reported. With an increase in scattering intensity by resonance Raman scattering (the intensity increase by the resonance Raman effect is typically about $10^3$ to $10^5$ times), Raman scattering has drawn attention. Resonance Raman is an effect of remarkably increasing the intensity of a Raman band derived from a vibration of a chromophore part corresponding to the absorption band when excitation light having a wavelength overlapping the absorption band of a certain molecule is used to measure Raman scattering. This enabled the Raman spectrum measurement of a pigment having a concentration of only several micromoles.

Then, in 1977, research groups of P. P. Van Duyne et al. (Non-Patent Document 5) and J. A. Creighton et al. (Non-Patent Document 6) independently found surface-enhanced Raman scattering. Three years before that, another research group of Fleischmann et al. actually observed the phenomenon, but they seemed to fail to recognize an increase in the scattering cross section as with the resonance Raman effect.

SERS generally means a phenomenon in which the Raman scattering intensity of a certain molecule adsorbed onto the surface of a metal electrode, sol, crystal, deposition film, or semiconductor is greatly enhanced compared with that of the molecule present in a solution. This phenomenon however still involves many unclear mechanisms. SERS is observed, for example, on gold, silver, copper, platinum, and nickel. A known feature of SERS is that the enhancement effect is especially large on silver and gold. The typical physical properties of SERS show the following dependencies.

1) The surface roughness of metal makes any contribution to expression of SERS.
2) An SERS spectrum typically shows clear wavelength dependence.
3) An SERS intensity depends on the orientation of molecules adsorbed on the surface of metal and also depends on the distance from the surface of the metal.

Two mechanisms have been proposed for expression of SERS so far. One of them is a surface plasmon model. Under this model, a reflectance spectrum is regarded as the absorption of surface plasmon generated by the collision of excitation light with the surface of metal and SERS occurs by a coupling between the molecular vibration of the adsorbed molecule and the surface plasmon excitation. The other model is called a charge transfer model. Under this model, a reflectance spectrum is regarded as the absorption of a complex formed by the surface of metal and a molecule and SERS occurs by the resonance Raman effect due to the absorption. In either case, although the mechanism has not been elucidated so far, it has been revealed that in the surface-enhanced Raman scattering in a condition satisfying both the resonance Raman condition and the SERS condition as described above, the scattering intensity increases by about $10^{11}$ to $10^{14}$ times. This greatly expands the potential of single molecule spectroscopy. Due to the high sensitivity, SERS has come to be applied to qualitative microanalysis.

As previously developed nanoparticles to be applied to SERS, for example, a method of adsorbing a low molecular aromatic ring compound onto the surface of a nanoparticle through direct electrostatic interaction and nanoparticles having a surface adsorbing a reporter molecule such as rhodamine, naphthalene, and quinoline having a thiol terminal (Non-Patent Document 7) have been applied as a molecular recognition sensor and a pH sensor (Non-Patent Document 8).

Examples of the known methods for synthesizing SERS particles include a method of synthesizing nano flake-like metal composite material (see Patent Document 1), a method of adsorbing a pigment (Raman active molecules) such as rhodamine 6G onto the surface of nano-porous material (see Patent Document 2), and a method using gold nanoparticles in which gold nanorods are immobilized onto a substrate and enhanced Raman scattering of the molecules on the surface is used for analysis (see Patent Document 3).

In addition, a plurality of synthesized organic-inorganic nanoclusters including a plurality of fused or aggregated metal particles that forms a metal cluster containing a plurality of Raman active organic compounds adsorbed onto the surfaces of a plurality of aggregated particles and to a plurality of junctions with which a plurality of metal particles firstly comes into contact is disclosed (see Patent Document 4).

RELATED ART DOCUMENTS

Patent Documents

Patent Document 1: Japanese Patent Application Publication No. 2009-061580 (JP 2009-061580 A)
Patent Document 2: Japanese Patent Application Publication No. 2008-184671 (JP 2008-184671 A)
Patent Document 3: Japanese Patent Application Publication No. 2005-233637 (JP 2005-233637 A)
Patent Document 4: Japanese Patent Application Publication No. 2007-514169 (JP 2007-514169 A)

Non-Patent Documents

Non-Patent Document 1: ACS Nano 2 (4) 612-616 (2008)
Non-Patent Document 2: Anal Chem, 79, 6927-6932 (2007)
Non-Patent Document 3: Anal Chem, 77, 6134-6139 (2005)
Non-Patent Document 4: J. Chem. Phys. 52, 399 (1970)
Non-Patent Document 5: J. Electroanal Chem., 84, 1 (1977)
Non-Patent Document 6: J. Am. Chem. Soc., 99, 5215 (1977)
Non-Patent Document 7: Langmuir 23, 10539-10545 (2007)
Non-Patent Document 8: Nano Lett. Vol. 7, No. 9, 2819-2823 (2007)
Non-Patent Document 9: J. Am. Chem. Soc. Vol. 131, 7518-7519 (2009)

SUMMARY OF THE INVENTION

Problem to be Solved by the Invention

In recent years, various applications of SERS have been studied. However, an applicable substrate and surface roughness are limited and the Raman intensity greatly depends on the orientation of Raman active molecules, which causes large variation depending on measurement position in many cases. SERS has therefore a disadvantage in that, for example, it is difficult to be applied to quantitative analysis.

When low molecular Raman active molecules such as a pigment that has been proposed are used, in an adsorption process (static adsorption process) of the Raman active molecules to nanoparticles, a surface charge of the nanoparticles changes. Then surface charge repulsion between the particles is reduced, which raises a problem of aggregation of the nanoparticles. The aggregation of the nanoparticles causes the desorption of the Raman active molecules. In addition, when the nanoparticles adsorbing Raman active molecules are aggregated before molecular recognition, SERS signals are generated even before the molecular recognition, which leads to false recognition. In particular, when such particles are used in a biological environment, dispersion stability in a high salt concentration must be ensured, and it is therefore required to take measures against the problem of the aggregation.

Means for Solving the Problem

As a result of repeated intensive studies in order to address the foregoing, the inventors of the present invention have found that, by forming a metal nanoparticle aggregate in which metal nanoparticles are connected to each other through organic molecules so as to be spaced apart a constant distance in advance, the coagulation of the metal nanoparticles and an unbalanced concentration distribution of the metal nanoparticles can be suppressed and surface-enhanced Raman scattering light obtained from an enhanced electric field generated on an adjacent interface between the metal nanoparticles can be stably detected.

The inventors of the present invention have also found that, by especially using DNA as the organic molecule that connects metal nanoparticles to each other, the distance between the metal nanoparticles can be easily made a desired distance and the aggregate of the metal nanoparticles can be readily produced, whereby the present invention has been accomplished.

That is, the present invention relates to, as a first aspect, a metal nanoparticle material for molecular sensing including a metal nanoparticle aggregate including three to ten metal nanoparticles connected to each other through an organic molecule so that adjacent metal nanoparticles are bonded and spaced apart a predetermined distance, and the aggregate contains a Raman active molecule within a field applied to the aggregate. The metal nanoparticle material emits enhanced Raman scattering light from the Raman active molecule in an enhanced electric field.

As a second aspect, the present invention relates to the metal nanoparticle material for molecular sensing according to the first aspect, in which the metal nanoparticles are of a metallic element having a resonance wavelength producing surface plasmon resonance in regions ranging from an ultraviolet region to an infrared region.

As a third aspect, the present invention relates to the metal nanoparticle material for molecular sensing according to the first aspect or the second aspect, in which the metal nanoparticles are particles having an average particle diameter of 1 nm to 100 nm.

As a fourth aspect, the present invention relates to the metal nanoparticle material for molecular sensing according to any one of the first aspect to the third aspect, in which, in the metal nanoparticle aggregate, the metal nanoparticles are not connected on a straight line to both adjacent metal nanoparticles.

As a fifth aspect, the present invention relates to the metal nanoparticle material for molecular sensing according to any one of the first aspect to the fourth aspect, in which the organic molecule has a terminal with a thiol group or an amino group and contains a nucleic acid, polyethylene glycol, or a hydrocarbon.

As a sixth aspect, the present invention relates to the metal nanoparticle material for molecular sensing according to the fifth aspect, in which the organic molecule is a nucleic acid having three to forty bases and having a terminal with a thiol group or an amino group.

As a seventh aspect, the present invention relates to the metal nanoparticle material for molecular sensing according to the sixth aspect, in which the nucleic acid is DNA.

As an eighth aspect, the present invention relates to the metal nanoparticle material for molecular sensing according to any one of the first aspect to the seventh aspect, in which the Raman active molecule is bonded to the organic molecule.

As a ninth aspect, the present invention relates to the metal nanoparticle material for molecular sensing according to any one of the first aspect to the eighth aspect, in which the metal nanoparticles are produced by bonding at least one molecular recognition probe molecule with the surfaces of the metal nanoparticles.

As a tenth aspect, the present invention relates to the metal nanoparticle material for molecular sensing according to any one of the first aspect to the ninth aspect, in which the molecular recognition probe molecule is a molecule having a terminal with a thiol group or an amino group and bonded with a molecular recognition probe through a nucleic acid, polyethylene glycol, or a hydrocarbon.

As an eleventh aspect, the present invention relates to a method for producing the metal nanoparticle material for molecular sensing as described in any one of the first aspect to the tenth aspect. The method includes:

a) associating a single-stranded nucleic acid strand (1) as a substrate with at least two single-stranded nucleic acid strands (2) each having complementarity to a partial base structure in the nucleic acid strand (1) and having one terminal with a thiol group to form a double helix, thereby obtaining a modified nucleic acid strand;

b) reacting the thiol groups in the modified nucleic acid strand with a metal nanoparticle to bond the modified nucleic acid strand onto the surface of the metal nanoparticle, and then heating the resulting product at 60 to 100° C. to dissociate the double helix structure of the modified nucleic acid strand, thereby removing the single-stranded nucleic acid strand (1) to obtain a metal nanoparticle (1) bonded with the single-stranded nucleic acid strands (2) through the thiol groups;

c) reacting a single-stranded nucleic acid strand (3) having complementarity to the nucleic acid strands (2), having one terminal with a thiol group, and having a base length equal to that of the nucleic acid strands (2) with a metal nanoparticle, thereby obtaining a metal nanoparticle (2) bonded with the single-stranded nucleic acid strand (3) through the thiol group;

d) mixing the metal nanoparticle (1) bonded with the single-stranded nucleic acid strands (2) and the metal nanoparticle (2) bonded with the single-stranded nucleic acid strand (3) to associate the single-stranded nucleic acid strands (2) with the single-stranded nucleic acid strand (3), thereby forming a double helix to produce a metal nanoparticle aggregate; and bonding a Raman active molecule to the single-stranded nucleic acid strands (2) used in a) and/or to the single-stranded nucleic acid strand (3) used in c).

As a twelfth aspect, the present invention relates to a method for producing the metal nanoparticle material for molecular sensing as described in any one of the first aspect to the tenth aspect. The method includes:

a) associating a single-stranded DNA strand (1) as a substrate with at least two single-stranded DNA strands (2) each having complementarity to a partial base structure in the DNA strand (1) and having one terminal with a thiol group to form a double helix, thereby obtaining a modified DNA strand;

b) reacting the thiol groups in the modified DNA strand with a metal nanoparticle to bond the modified DNA strand onto the surface of the metal nanoparticle, and then heating the resulting product at 60 to 100° C. to dissociate the double helix structure of the modified DNA strand, thereby removing the single-stranded DNA strand (1) to obtain a metal nanoparticle (1) bonded with the single-stranded DNA strands (2) through the thiol groups;

c) reacting a single-stranded DNA strand (3) having complementarity to the DNA strands (2), having one terminal with a thiol group, and having a base length equal to that of the DNA strands (2) with a metal nanoparticle, thereby obtaining a metal nanoparticle (2) bonded with the single-stranded DNA strand (3) through the thiol group;

d) mixing the metal nanoparticle (1) bonded with the single-stranded DNA strands (2) and the metal nanoparticle (2) bonded with the single-stranded DNA strand (3) to associate the single-stranded DNA strands (2) with the single-stranded DNA strand (3), thereby forming a double helix to produce a metal nanoparticle aggregate; and bonding a Raman active molecule to the single-stranded DNA strands (2) used in a) and/or to the single-stranded DNA strand (3) used in c).

As a thirteenth aspect, the present invention relates to the method for producing the metal nanoparticle material for molecular sensing according to the twelfth aspect, in which, in d), 2 equivalents of the metal nanoparticle (2) bonded with the single-stranded DNA strand (3) is used with respect to 1 equivalent of the metal nanoparticle (1) bonded with the single-stranded DNA strands (2) to produce the metal nanoparticle aggregate.

As a fourteenth aspect, the present invention relates to the method for producing the metal nanoparticle material for molecular sensing according to the twelfth aspect or the thirteenth aspect, in which the single-stranded DNA strands (2) do not have a part complementary to each other.

As a fifteenth aspect, the present invention relates to the method for producing the metal nanoparticle material for molecular sensing according to any one of the twelfth aspect to the fourteenth aspect. The method further includes, in any of a) to d):

e) reacting the metal nanoparticles with a molecular recognition probe molecule which includes a molecular chain containing a nucleic acid, polyethylene glycol, or a hydrocarbon, the molecular chain having one terminal with a molecular recognition probe and having another terminal with a thiol group or an amino group, thereby bonding the molecular recognition probe molecule at the terminal to the surfaces of the metal nanoparticles through the thiol group or the amino group.

As a sixteenth aspect, the present invention relates to a molecular sensing method characterized by including bringing the metal nanoparticle material for molecular sensing as described in any one of the first aspect to the tenth aspect into contact with a specimen, and then performing Raman scattering measurement of the specimen.

As a seventeenth aspect, the present invention relates to the molecular sensing method according to the sixteenth aspect, in which the metal nanoparticle material for molecular sensing is immobilized onto a substrate.

Effects of the Invention

A metal nanoparticle material for molecular sensing of the present invention includes a metal nanoparticle aggregate in which metal nanoparticles are connected and spaced apart a predetermined distance. Hence, the metal nanoparticle material enables an enhanced electric field intensity formed on an interface of the metal nanoparticles to be constant, can prevent a false detection that has been a problem in related art and that is caused by the coagulation of SERS particles or an unbalanced concentration distribution, and can avoid the variation in SERS signals due to a surface condition, which leads to stable detection of surface-enhanced Raman scattering light.

The metal nanoparticle material for molecular sensing of the present invention enables an intended specimen to be detected by connecting a molecular recognition probe such as biotin onto the surfaces of the metal nanoparticles of the metal nanoparticle aggregate.

The use of the metal nanoparticle material for molecular sensing of the present invention enables the surface-enhanced Raman scattering intensity that reaches $10^{11}$ times a common Raman scattering intensity to be stably maintained. Therefore, a specimen having an extremely low concentration can be detected.

By the method for producing the metal nanoparticle material for molecular sensing of the present invention, by simply mixing metal nanoparticles such as gold nanoparticles, silver nanoparticles, copper nanoparticles, platinum nanoparticles, or nickel nanoparticles that are particles having surface-enhanced Raman scattering activity and that are modified with a single-stranded DNA strand having a terminal with a thiol group or an amino group, and such metal nanoparticles modified with another single-stranded DNA that is complementary to the DNA strand and that has a terminal with a thiol group, a bond is readily formed between the metal nanoparticles, and as a result, a metal nanoparticle aggregate can be produced.

The distance between the metal nanoparticles can be freely controlled by adjusting the number of DNA bases, and this enables the production of a metal nanoparticle aggregate in which the metal nanoparticles are connected to each other and spaced apart a distance capable of generating the highest enhanced electric field.

In addition, by connecting, to a metal nanoparticle surface in the metal nanoparticle aggregate, a molecule (molecular recognition probe molecule) having strong interaction with respect to an intended specimen, SERS active molecular recognition particles capable of recognizing the intended specimen can be synthesized.

BRIEF DESCRIPTION OF THE DRAWINGS

FIG. 21 is a view showing ultraviolet-visible absorption spectra of a sample [3] solution (DNA 13), a sample [4] (DNA 14) solution, and a sample [5] solution (DNA 15) obtained in Case 10 (DNA 13: sign 19, DNA 14: sign 20, DNA 15: sign 21).

FIG. 22 is a view showing each appearance (photograph) of a sample [6] and a sample [7] obtained in Case 10.

FIG. 23 is a view showing the result of resonance Raman scattering measurement of an AS1411-adsorbed gold nanoparticle aggregate.

FIG. 26 is views showing a mapping derived from phosphoric acid of DNA derived from the cancer cells, a mapping of a gold particle adsorbed area, and a micrograph of the cancer cells.

MODES FOR CARRYING OUT THE INVENTION

Figure 1:
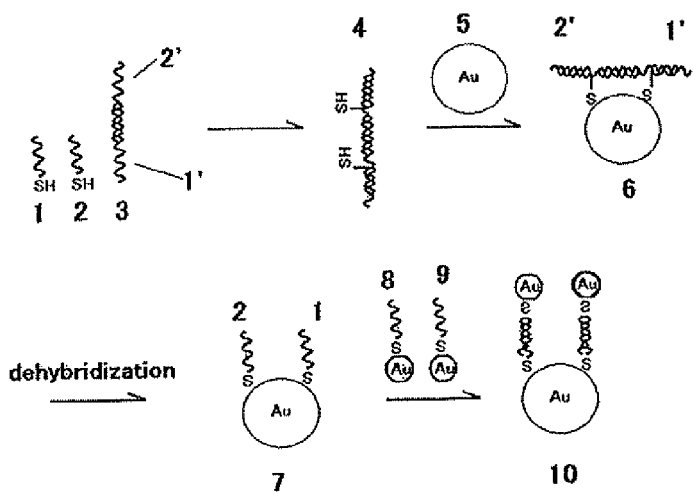
FIG. 1 is a view showing a production scheme of a metal nanoparticle material for molecular sensing of the present invention.

A metal nanoparticle material for molecular sensing of the present invention includes a metal nanoparticle aggregate including three to ten metal nanoparticles which are connected to each other through an organic molecule, the adjacent metal nanoparticles are bonded while being spaced apart a predetermined distance, and the aggregate contains a Raman active molecule within an electric field applied to the aggregate.

The metal nanoparticles used in the present invention are not particularly limited but are of a metallic element having a resonance wavelength producing surface plasmon resonance in regions ranging from an ultraviolet region to an infrared region. Examples of the metal nanoparticles include particles composed of a metallic element selected from, for example, gold, silver, copper, platinum, nickel, and aluminum. Among them, gold nanoparticles are preferably used.

It is desirable that the metal nanoparticles have an average particle diameter of 1 nm to 500 nm, preferably 1 nm to 100 nm, more preferably 5 nm to 100 nm, and particularly preferably 5 nm to 20 nm.

As the organic molecule used for connecting the metal nanoparticles to each other, a molecular chain including an organic compound such as a nucleic acid, polyethylene glycol, or a hydrocarbon may be used. Such an organic molecule has a terminal with a thiol group or an amino group that is a group for making a bond to a metal nanoparticle (surface).

Among them, a nucleic acid (specifically, DNA) is particularly preferred because the controlling of the number of bases enables an organic molecule to have a desired molecular chain length, that is, such controlling enables the distance between the metal nanoparticles to be easily adjusted to a desired length. In this case, the number of bases of the nucleic acid is preferably in a range from 3 bases to 40 bases and more preferably 3 to 20 bases, and, for example, DNA having 12 bases is preferably used.

It is preferable that the organic molecule include, in addition to the compound (such as DNA) used for adjusting the distance between the metal nanoparticles to a predetermined distance, the Raman active molecule (also called Raman probe) that is bonded to the organic molecule. Examples of the Raman active molecule include, besides organic pigment molecules such as rhodamine 6G (R6G), crystal violet (CRV), and coumarin, condensed-ring compounds having some aromatic rings that are fused. Such a Raman active molecule is introduced to a terminal of any organic molecule.

The number of the metal nanoparticles to be connected through the organic molecule is preferably three to ten as described above. The reason for this is as follows. An enhanced electric field induced between two adjacent metal particles is oriented in various directions due to the movement of two particles, and thus is not constantly oriented in a direction to generate an optimum enhanced magnetic field. Hence, in order to generate an optimum enhanced electric field even when particles move, it is desirable to form an aggregate including three or more particles in which a particle is further bonded through an organic molecule in a bond direction having an angle of 180° or less with respect to the bond direction of another organic molecule formed between two particles. However, even when an aggregate including additional organic molecules and metal particles is bonded to such an aggregate including three particles, the formed aggregate is not preferable because it causes the difference in concentration at a labeled part during detection. The metal particle aggregate preferably includes up to about 10 metal particles that are bonded through organic molecules. In the metal nanoparticle aggregate, it is preferable that the metal nanoparticles be not connected on a straight line to both adjacent metal nanoparticles, that is, two organic molecules between three metal nanoparticles be bonded to the center metal nanoparticle to have an angle of 180° or less, for example, 10 to 160°.

The metal nanoparticle (surface) in the metal nanoparticle aggregate may further has a molecular recognition probe molecule capable of recognizing an intended specimen. This enables an intended specimen to be detected by the measurement of Raman scattering after the recognition of the specimen.

The molecular recognition probe molecule is, for example, a molecule including a molecular chain that contains a nucleic acid (DNA) having a base sequence different from that of the nucleic acid (DNA) used as the organic molecule described above, polyethylene glycol, or a hydrocarbon, that has one teiininal to which a molecular recognition probe (such as biotin; also called detection part) is introduced, and that has another terminal to which a group capable of bonding to the surface of a metal nanoparticle, such as a thiol group and an amino group is introduced. Then, the molecular recognition probe molecule is bonded to a metal nanoparticle (surface) through the thiol group or the like.

A method for producing the metal nanoparticle material for molecular sensing of the present invention includes processes a) to d) below:

a) a process of associating a single-stranded nucleic acid strand (1) as a substrate with at least two single-stranded nucleic acid strands (2) that have complementarity to a partial base structure in the nucleic acid strand (1) and have one terminal with a thiol group to form a double helix, thereby obtaining a modified nucleic acid strand;

b) a process of reacting the thiol groups in the modified nucleic acid strand with a metal nanoparticle to bond the modified nucleic acid strand onto the surface of the metal nanoparticle, and then heating the product at 60 to 100° C. to dissociate the double helix structure of the modified nucleic acid strand, thereby removing the single-stranded nucleic acid strand (1) to obtain a metal nanoparticle (1) bonded with the single-stranded nucleic acid strands (2) through the thiol groups;

c) a process of reacting a single-stranded nucleic acid strand (3) that has complementarity to the nucleic acid strands (2), has one terminal with a thiol group, and has a base length equal to that of the nucleic acid strands (2) with a metal nanoparticle, thereby obtaining a metal nanoparticle (2) bonded with the single-stranded nucleic acid strand (3) through the thiol group; and d) a process of mixing the metal nanoparticle (1) bonded with the single-stranded nucleic acid strands (2) and the metal nanoparticle (2) bonded with the single-stranded nucleic acid strand (3) to associate the single-stranded nucleic acid strands (2) with the single-stranded nucleic acid strand (3), thereby forming a double helix to produce a metal nanoparticle aggregate.

In the method for producing the metal nanoparticle material for molecular sensing of the present invention, the nucleic acid is preferably DNA. In other words, a method for producing the metal nanoparticle material for molecular sensing includes processes a) to d) below:

a) a process of associating a single-stranded DNA strand (1) as a substrate with at least two single-stranded DNA strands (2) that have complementarity to a partial base structure in the DNA strand (1) and have one terminal with a thiol group to form a double helix, thereby obtaining a modified DNA strand;

b) a process of reacting the thiol groups in the modified DNA strand with a metal nanoparticle to bond the modified DNA strand onto the surface of the metal nanoparticle, and then heating the product at 60 to 100° C. to dissociate the double helix structure of the modified DNA strand, thereby removing the single-stranded DNA strand (1) to obtain a metal nanoparticle (1) bonded with the single-stranded DNA strands (2) through the thiol groups;

c) a process of reacting a single-stranded DNA strand (3) that has complementarity to the DNA strands (2), has one terminal with a thiol group, and has a base length equal to that of the DNA strands (2) with a metal nanoparticle, thereby obtaining a metal nanoparticle (2) bonded with the single-stranded DNA strand (3) through the thiol group; and d) a process of mixing the metal nanoparticle (1) bonded with the single-stranded DNA strands (2) and the metal nanoparticle (2) bonded with the single-stranded DNA strand (3) to associate the single-stranded DNA strands (2) with the single-stranded DNA strand (3), thereby forming a double helix to produce a metal nanoparticle aggregate.

The method for producing the metal nanoparticle material for molecular sensing of the present invention further includes, in addition to the processes a) to d), a process of bonding a Raman active molecule to the single-stranded DNA strands (2) used in the process a) and/or to the single-stranded DNA strands (3) used in the process c).

The single-stranded DNA strands (2) used in the process may have complementarity to each other but preferably do not have complementarity to each other. This is because when the DNA strands (2) having complementarity to each other are reacted with a metal nanoparticle to form a metal nanoparticle (1) bonded with the single-stranded DNA strands (2), the particles (1) may be associated to each other to form an aggregate. The DNA strands (2) not having complementarity to each other can suppress the coagulation.

The single-stranded DNA strands (2) may have a different molecular chain length (namely, base length) from that of the single-stranded DNA strands (3) but preferably have an equal molecular chain length to that of the single-stranded DNA strands (3).

The metal used for the metal nanoparticle (1) and the metal used for the metal nanoparticle (2) used in the processes may be the same or different from each other. Preferably, the same metal species is desirably used.

The distance between the two thiol groups in two DNA strands (2) that are associated with the single-stranded DNA strand (1) as a substrate in the process a) corresponds to the bonding positions of the DNA strands (2) to be formed on the metal nanoparticle (1) obtained in the process b).

Here, if the two DNA strands (2) are bonded to the opposed positions while interposing the metal nanoparticle therebetween, three metal nanoparticles will be aligned on a straight line, that is, the DNA strands (2) will be associated with the DNA strand (3) in the following process d), which aligns three particles of the metal nanoparticle (1) and two metal nanoparticles (2). In other words, two enhanced electric fields formed between these three metal nanoparticles form an angle of 180° and this is not preferable as described above.

On this account, it is important to control the length of a DNA strand or the size of metal nanoparticles (average particle diameter) for adjusting the arrangement (angle) of three metal nanoparticles to a preferred angle.

The process d), that is, the process of mixing the metal nanoparticle (1) with the metal nanoparticle (2) to produce a metal nanoparticle aggregate is performed by adding an excess amount of the metal nanoparticle (2) to the metal nanoparticle (1). For example, by mixing the metal nanoparticles (1) and the metal nanoparticles (2) in an equivalent ratio of about 1:2 to 10, the DNA strand (2) and the DNA strand (3) are associated to form a double helix, thereby forming a bond of an organic molecule (such as DNA) between two metal nanoparticles.

For example, a metal nanoparticle (1) having 2 equivalents of single-stranded DNA strand (2) is mixed with two metal nanoparticles (2) each having 1 equivalent of single-stranded DNA strand (3) to afford a preferred metal nanoparticle aggregate including three metal nanoparticles.

The metal nanoparticle aggregate that is obtained in this manner and in which metal nanoparticles are connected while being spaced at equal intervals works as a molecular sensing metal nanoparticle material capable of generating surface-enhanced Raman scattering.

Hereinafter, a method for producing a metal nanoparticle aggregate used in the metal nanoparticle material for molecular sensing of the present invention will be described with reference to a specific example in FIG. 1. The method can be performed in accordance with the method described in Non-Patent Document 9.

Three samples of DNA represented by 1, 2, and 3 in FIG. 1 (hereinafter, called DNA 1, DNA 2, and DNA 3, respectively) are prepared. The DNA 1 and the DNA 2 are complementary to each other. The DNA 3 is a base chain having a double-stranded central part but having both terminals that have complementarity to the DNA 1 and the DNA 2. Each of the DNA 1 and the DNA 2 has a terminal with a thiol group.

The DNA 1, the DNA 2, and the DNA 3 are mixed to synthesize a modified DNA 4 shown in FIG. 1. The synthesized modified DNA 4 is mixed with a colloidal solution of gold nanoparticles 5 to be bonded to the surface of a gold nanoparticle through the thiol group, resulting in a gold nanoparticle 6 bonded with DNA shown in FIG. 1. Next, the solution is heated (the temperature is appropriately designed depending on the number of bases) to dissociate the double strand, which synthesizes a gold nanoparticle 7 bonded with the DNA 1 and the DNA 2 shown in FIG. 1.

Then, gold nanoparticles 8 and 9 in which the DNA 1 and the DNA 2 containing a Raman active molecule are previously bonded to the surfaces of gold nanoparticles through a thiol group are added to the gold nanoparticle 7 shown in FIG.

1, which associates the DNAs to each other to form double-strands. As a result, a gold particle conjugation 10 shown in FIG. 1 is completed. In this case, each gold particle can be immobilized at a completely controlled position.

The metal nanoparticle material for molecular sensing of the present invention is brought into contact with a specimen, and then the specimen is subjected to Raman scattering measurement. As a result, the method is useful for molecular sensing.

At this time, the metal nanoparticle material for molecular sensing may be immobilized onto a substrate.

The metal nanoparticle material for molecular sensing of the present invention uses, as described above, a metal nanoparticle aggregate in which metal nanoparticles are bonded while being spaced apart a predetermined distance. Thus, the metal nanoparticle material can control an enhanced electric field formed on an interface of the metal nanoparticles. In other words, a stable enhanced electric field can be formed on the surfaces of metal nanoparticles, thereby stabilizing a constant Raman scattering intensity. Therefore, this is a very useful technique for improving unstable Raman scattering as in related art.

EXAMPLES

The present invention will now be specifically described in detail with reference to examples but the present invention is not limited to them.

In the base sequences below, adenine is abbreviated as (A), guanine is abbreviated as (G), thymine is abbreviated as (T), cytosine is abbreviated as (C), and a thiol group is abbreviated as (HS or SH).

[Case 1: Immobilization of Thiol-Terminated DNA to Gold Nanoparticles]

First, single-stranded DNAs (a) and (b) complementary to each other were prepared.

(a) 5'-HS-C6-GCCACCAGCTCC-C6-TAMRA-3' (SEQ ID NO: 1)

In a 12-base DNA having a base sequence of GCCACCAGCTCC (SEQ ID NO: 1), a thiol group to be immobilized to a gold surface was bonded to the 5' terminal through a C6 alkyl chain (C6) and rhodamine (TAMRA) as a pigment is bonded to the 3' terminal through a C6 alkyl chain (C6) as a Raman active molecule (Raman probe).

(b) 5'-HS-C6-GGAGCTGGTGGC-3' (SEQ ID NO: 2)

In a 12-base DNA having a base sequence of GGAGCTGGTGGC (SEQ ID NO: 2), a thiol group to be immobilized to a gold surface was bonded to the 5' terminal through a C6 alkyl chain (C6).

These single-stranded DNAs (a) and (b) are independently added to a gold nanoparticle solution (colloidal gold solution), thereby being bonded to the surface of a gold nanoparticle. However, each terminal thiol group in the DNAs is unstable and surrounding thiol groups are bonded to each other to readily form an S—S bond. Hence, the formed S—S bond is required to be reduced to a thiol group with a reducing agent before the DNAs are immobilized to a gold surface. The reduction method is not particularly limited but, as an example, in this case, the S—S bond was reduced by the following procedure.

In other words, 50 µL of 100 pmol/µL 5'-thiolated DNA solution in DTT (dithiothreitol) was charged in a 1.5-mL microtube, then 20 µL of 2.5 M NaCl and 950 µL of ethanol cooled at −20° C. were added, and the mixture was left at −80° C. for 20 minutes. Then, the reaction mixture was centrifuged at 12,000 rotations at 4° C. for 10 minutes, then a supernatant liquid was discarded, and the residue was redissolved with 50 µL of TE solution (tris-EDTA buffer: 10 mM tris-hydroxymethylaminomethane, 1 mM EDTA, a pH of less than 8), which afforded a purified thiolated DNA.

The immobilizing (bonding) operation of the DNA to gold nanoparticles is not particularly limited but, in this case, was carried out by the following manner.

In other words, to 1 mL of gold nanoparticle solution, 5 nmol of the purified thiolated DNA in which the S—S bond had been reduced by the procedure described above was added. At this time, the final concentration of the thiolated DNA was 5 µL.

After the addition, the container was stirred for 5 minutes with a vortex mixer, and then was left in a constant temperature chamber at 50° C. for 4 to 24 hours, thereby the immobilization of the DNA onto the surface of a gold nanoparticle was accelerated. At this time, onto the surface of the gold nanoparticle, not only the thiol group was bonded but also the DNA base was adsorbed. Thus, the surface was not in a tight adsorption state. Hence, to a solution of gold nanoparticles and thiolated DNA, 40 µL of 2.5 M NaCl and 20 µL of 500 mM phosphate buffer were added so that NaCl and the phosphate buffer (pH 7) would have final concentrations of 0.1 M and 10 mM, respectively, and the mixture was further left at 50° C. for 40 hours.

[Case 2: Production of Gold Nanoparticle Aggregate]

Each 0.5 mL of two kinds of solutions of the gold nanoparticles to which the corresponding DNAs complementary to each other were immobilized by the procedure described above was charged in a microtube. The solution was centrifuged at 14,000 rpm for 25 minutes, then a supernatant liquid was removed, and the residue was redispersed with a 10 mM phosphate buffer (containing 0.1 M NaCl, pH 7). At this time, the dispersion liquid was sometimes falsely aggregated. In such a case, the liquid was warmed at 50° C. for a while for redispersion. The operation was repeated once more, then the supernatant liquid was removed, and the residue was redispersed in 1 µL of 0.01% tween-20 and 0.25 mL of 0.1 M NaCl (10 mM phosphate buffer, pH 7).

Two kinds of dispersion solutions of the gold nanoparticles that had surfaces bonded with the DNAs and were obtained in this manner, were mixed and the complementary DNA strands were associated, which formed a bond between the gold nanoparticles to produce a metal nanoparticle aggregate.

In other words, first, into a PCR tube, 1 µL of 1% tween-20, 5 µL of DNA modified gold nanoparticles (each 5 µL of modified particles complementary to each other), and 4 µL of 5 M NaCl were charged and the mixture was left at room temperature for 10 minutes. When the formation of a gold nanoparticle aggregate (looking like a conglomerate) was not observed, the mixture was left on ice for 20 minutes or more. Then, the mixture was lightly centrifuged with a desktop centrifuge, and the obtained aggregate was precipitated.

A gold nanoparticle aggregate could also be obtained by the following procedure. First, into a PCR tube, 1 µL of 1% tween-2, 5 µL of DNA modified gold nanoparticles, 10 µL of 1 µM DNA complementary to the DNA used for the modification, and 4 µL of 5 M NaCl were charged, and the mixture was left at room temperature for 10 minutes, (when the formation of a gold nanoparticle aggregate (looking like a conglomerate) was not observed, the mixture was left on ice for 20 minutes or more), and then the mixture was lightly centrifuged with a desktop centrifuge, which precipitated the obtained aggregate.

[Case 3: Analysis of Gold Nanoparticle Aggregate (1): Analysis of Aggregate Formation]

The metal nanoparticle aggregate obtained was analyzed under a transmission electron microscope and an atomic force microscope.

Figure 2:
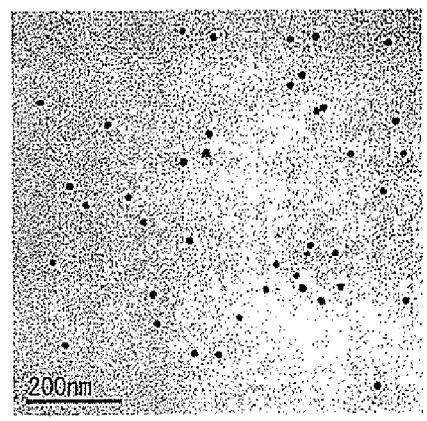
FIG. 2 is a view showing a transmission electron microscope image of 5'-HS-C6-GCCACCAGCTCC-C6-TAMRA-3' (SEQ ID NO: 1) surface-modified gold nanoparticles.
Figure 3:
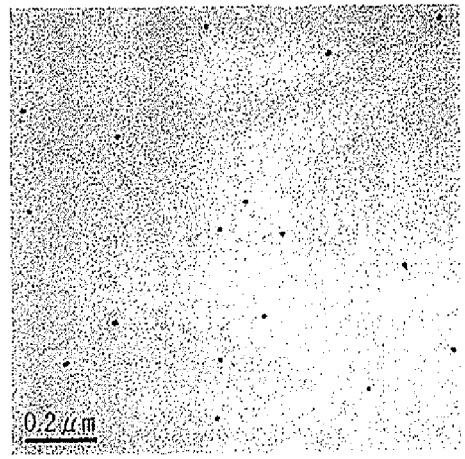
FIG. 3 is a view showing a transmission electron microscope image of 5'-HS-C6-GGAGCTGGTGGC-3' (SEQ ID NO: 2) surface-modified gold nanoparticles.
Figure 4:
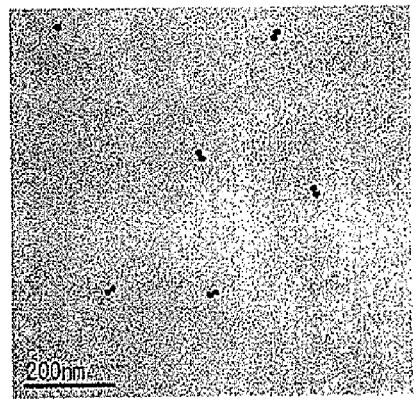
FIG. 4 is a view showing a transmission electron microscope image of a particle state after mixing the 5'-HS-C6-GCCACCAGCTCC-C6-TAMRA-3' (SEQ ID NO: 1) surface-modified gold nanoparticles and the 5'-HS-C6-GGAGCTGGTGGC-3' (SEQ ID NO: 2) surface-modified gold nanoparticles.

FIG. 2 shows a transmission electron microscope image of the gold nanoparticles bonded with the single-stranded DNA (a) [5'-HS-C6-GCCACCAGCTCC-C6-TAMRA-3' (SEQ ID NO: 1)], FIG. 3 shows a transmission electron microscope image of the gold nanoparticles bonded with the single-stranded DNA (b) [5'-HS-C6-GGAGCTGGTGGC-3' (SEQ ID NO: 2)], and FIG. 4 shows a transmission electron microscope image of the gold nanoparticle aggregate obtained by mixing these gold nanoparticles.

Figure 5:
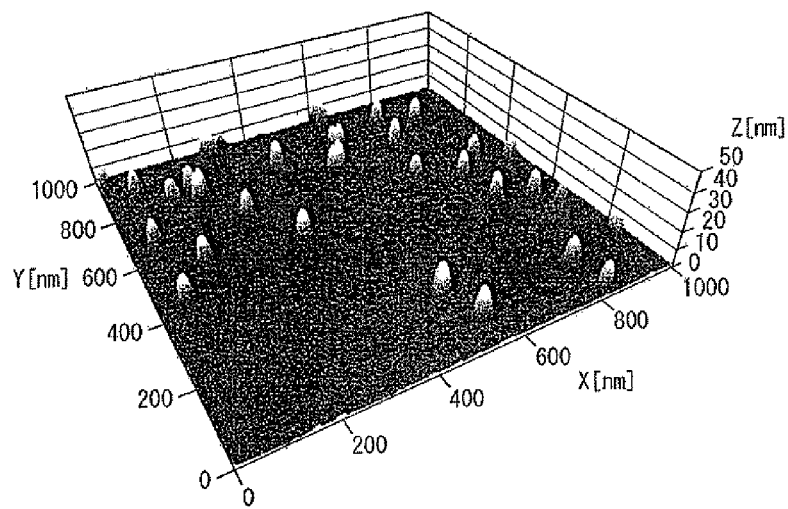
FIG. 5 is a view showing an atomic force microscope image of gold nanoparticles to which 5'-HS-C6-GGAGCTGGTGGC-3' (SEQ ID NO: 2) is immobilized.
Figure 6:
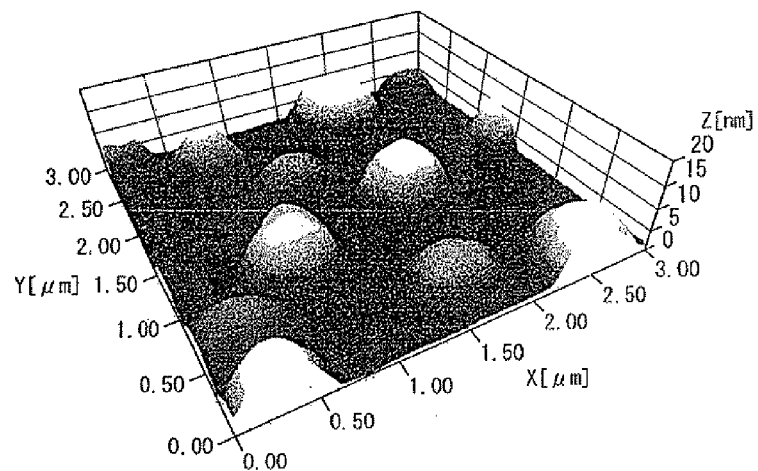
FIG. 6 is a view showing an atomic force microscope image of particles after mixing the 5'-HS-C6-GCCACCAGCTCC-C6-TAMRA-3' (SEQ ID NO: 1) surface-modified gold nanoparticles and the 5'-HS-C6-GGAGCTGGTGGC-3' (SEQ ID NO: 2) surface-modified gold nanoparticles.

FIG. 5 shows an atomic force microscope image of the gold nanoparticles bonded with the single-stranded DNA (b) [5'-HS-C6-GGAGCTGGTGGC-3' (SEQ ID NO: 2)] and FIG. 6 shows an atomic force microscope image of the gold nanoparticle aggregate obtained by mixing the gold nanoparticles bonded with the single-stranded DNA (b) and the gold nanoparticles bonded with the single-stranded DNA (a) [5'-HS-C6-GCCACCAGCTCC-C6-TAMRA-3' (SEQ ID NO: 1)].

As shown in FIG. 4 and FIG. 6, it was ascertained that the aggregate could be formed by mixing two types of gold nanoparticles in a monodispersed state from the transmission electron microscope image and the atomic force microscope image.

[Case 4: Analysis of Gold Nanoparticle Aggregate (2): Measurement of Enhanced Field]

Next, the measurement of an enhanced electric field formed on an interface of adjacent gold nanoparticles and the shape measurement were simultaneously carried out under a near-field microscope.

Figure 7:
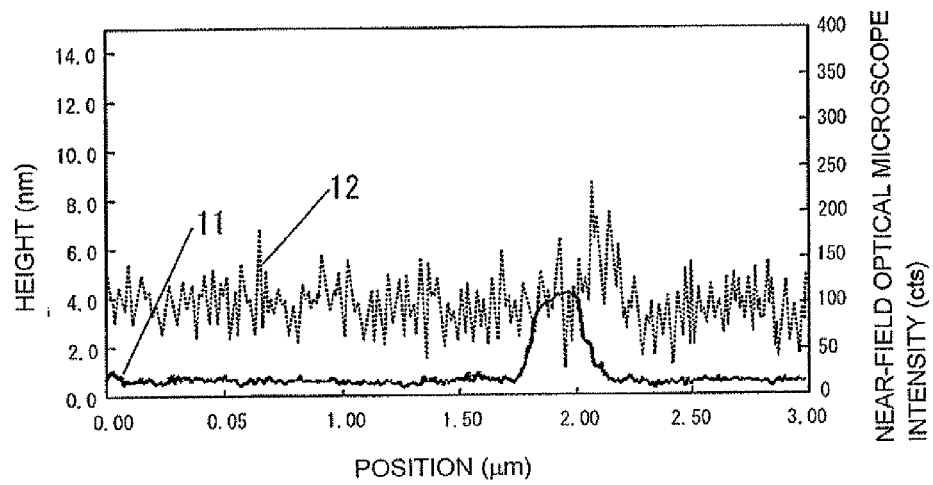
FIG. 7 is a view showing the shape and the electric field measurement of the gold nanoparticles to which 5'-HS-C6-GGAGCTGGTGGC-3' (SEQ ID NO: 2) is immobilized, under a near-field optical microscope.
Figure 8:
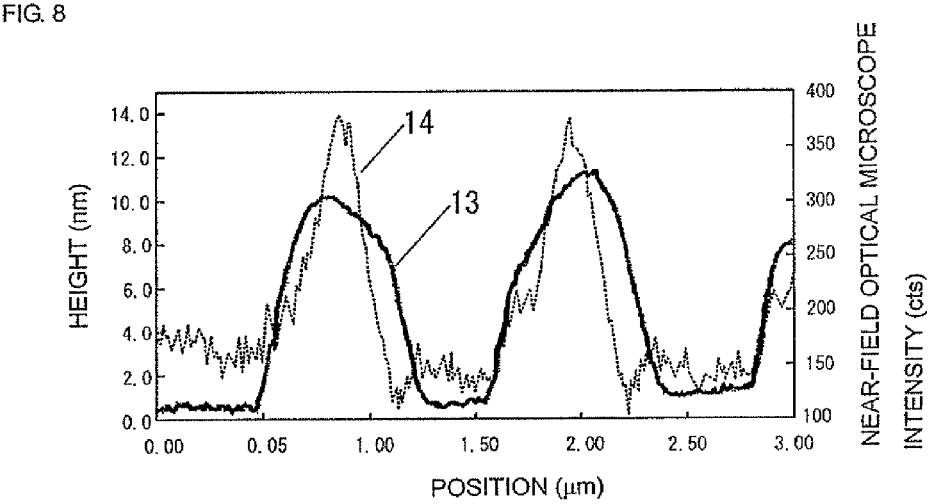
FIG. 8 is a view showing the shape and electric field measurement of the particles after mixing the 5'-HS-C6-GCCACCAGCTCC-C6-TAMRA-3' (SEQ ID NO: 1) surface-modified gold nanoparticles and the 5'-HS-C6-GGAGCTGGTGGC-3' (SEQ ID NO: 2) surface-modified gold nanoparticles, under a near-field optical microscope.

FIG. 7 shows a near-field microscope image (position information, the sign 11 in FIG. 7) of the gold nanoparticles bonded with the single-stranded DNA (b) [5'-HS-C6-GGAGCTGGTGGC-3' (SEQ ID NO: 2)] and an electric field (the sign 12 in FIG. 7) formed near the surface, and FIG. 8 shows a near-field microscope image (position information, the sign 13 in FIG. 8) of the gold nanoparticle aggregate obtained by mixing the gold nanoparticles bonded with the single-stranded DNA (b) and the gold nanoparticles bonded with the single-stranded DNA (a) [5'-HS-C6-GCCACCAGCTCC-C6-TAMRA-3' (SEQ ID NO: 1)] and an electric field (the sign 14 in FIG. 8) formed near the surface.

As shown in FIG. 7 and FIG. 8, it was ascertained that very strong enhanced electric fields were obtained from the particles forming the gold nanoparticle aggregate. From the result, it can be expected that very strong Raman scattering can be obtained from the Raman active molecule included in the enhanced electric field.

[Case 5: Analysis of Gold Nanoparticle Aggregate (3): Raman Spectrum Measurement]

Subsequently, the obtained gold nanoparticle aggregate (solution) was sealed in a quartz capillary tube and a Raman spectrum of the solution in the capillary tube was measured. The 12-base DNA used in the test was dissociated at a temperature of 90° C. or more to be returned to single-stranded DNA. Hence, the Raman spectrum was also measured at a temperature of 90° C. The sign 15 in FIG. 9 shows the Raman spectrum result (gold nanoparticle aggregate) measured at a temperature (about 34 to 38° C.) corresponding to a biological temperature and the sign 16 in FIG. 9 shows the Raman spectrum result (gold nanoparticles bonded with single-stranded DNA) measured at a temperature of 90° C.

Figure 9:
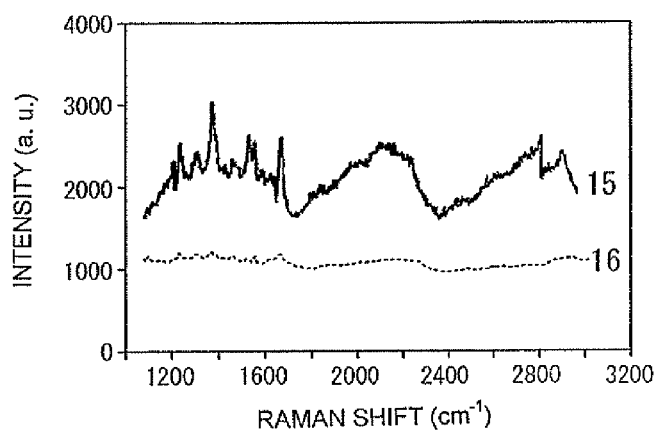
FIG. 9 is a view showing a resonance Raman scattering measurement result of the particles after mixing the 5'-HS-C6-GCCACCAGCTCC-C6-TAMRA-3' (SEQ ID NO: 1) surface-modified gold nanoparticles and the 5'-HS-C6-GGAGCTGGTGGC-3' (SEQ ID NO: 2) surface-modified gold nanoparticles.
Figure 10:
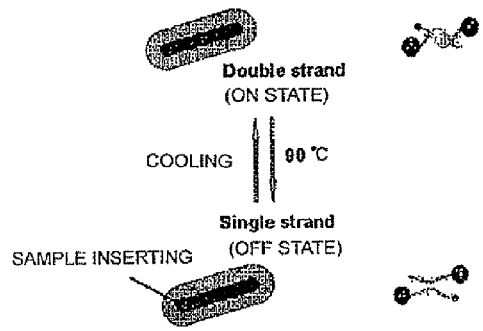
FIG. 10 is a view showing a schematic diagram of Raman scattering intensity change of the particles after mixing the 5'-HS-C6-GCCACCAGCTCC-C6-TAMRA-3' (SEQ ID NO: 1) surface-modified gold nanoparticles and the 5'-HS-C6-GGAGCTGGTGGC-3' (SEQ ID NO: 2) surface-modified gold nanoparticles, due to temperature change.

As revealed by FIG. 9, strong Raman scattering was observed from the gold nanoparticles forming the aggregate. This is supposed to be because the gold nanoparticles were reversibly associated (aggregated) and dissociated to each other depending on the variation in temperature as shown in FIG. 10.

[Case 6: Production of Molecular Recognition Probe-Containing Gold Nanoparticle Aggregate and Molecular Recognition]

The surfaces of metal nanoparticles of the gold nanoparticle aggregate obtained in this manner were further modified with a molecular recognition probe capable of recognizing a particular molecule. The method is not particularly limited but a molecular recognition probe is typically mixed before the immobilization of the DNA to the surfaces of gold nanoparticles shown above.

In other words, first, into a PCR tube, 1 μL of 1% tween-20, 5 μL of DNA modified gold nanoparticles, a solution in which a hetero bifunctional PEG (a molecular weight of 5,000) having one terminal with an alkylamine and the other terminal with biotin was mixed at a ratio of 10% by mass in 10 μL of 1 μM DNA complementary to the DNA used for the modification of the DNA modified gold nanoparticles, and 4 μL of 5 M NaCl were added, then the mixture was left at room temperature for 10 minutes, (when the formation of a gold nanoparticle aggregate (looking like a conglomerate) was not observed, the mixture was left on ice for 20 minutes or more), and then the mixture was slightly centrifuged with a desktop centrifuge, which precipitated an aggregate.

Figure 11:
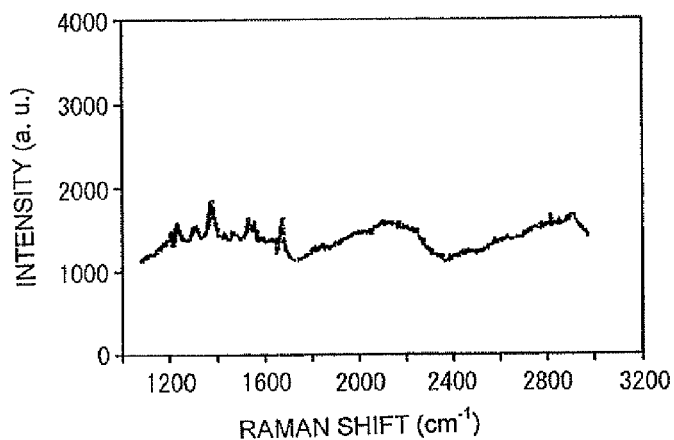
FIG. 11 is a view showing of the molecular recognition of streptavidin by 5'-HS-C6-GCCACCAGCTCC-C6-TAMRA-3' (SEQ ID NO: 1) surface-modified gold nanoparticles having a surface to which biotin is introduced as a sensing probe and the 5'-HS-C6-GGAGCTGGTGGC-3' (SEQ ID NO: 2) surface-modified gold nanoparticles.

The molecular recognition probe-containing gold nanoparticle aggregate for Raman sensing obtained in this manner was applied to a streptavidin plate. The plate was left at room temperature for several minutes, and then was washed with sterile water several times, thereby the molecular recognition probe-containing gold nanoparticle aggregate for Raman sensing that was not immobilized was sufficiently washed until the plasmon absorption of gold disappeared from the washing water. The streptavidin plate treated in this manner was observed under a laser Raman microscope to afford a Raman scattering spectrum as shown in FIG. 11, and this revealed that the molecular recognition probe-containing gold nanoparticle aggregate for Raman sensing could perform the molecular recognition.

Experimental Example 1

Production of Gold Nanoparticle Aggregate and Molecular Recognition

<Preparation of DNA>

Two kinds of single-stranded DNAs were prepared.

First, in a 33-base DNA having a base sequence of TTTCTATTCCTA CCAATGTAGCGACTACCTCAG (SEQ ID NO: 3), a thiol group to be immobilized to a gold surface was bonded to the 5' terminal through a C6 alkyl chain, which synthesized DNA.

Separately, in a 33-base DNA having a base sequence of TTTCGATCTAATACAGTTAGTTAGTATACGTGC (SEQ ID NO: 4), a thiol group to be immobilized to a gold surface was bonded to the 5' terminal through a C6 alkyl chain, which synthesized DNA.

Next, as a single-stranded DNA as a template for immobilizing two single-stranded DNAs described above to a metal nanoparticle, a single-stranded DNA having a base group complementary to the single-stranded DNA and a base group for controlling the distance between the two single-stranded DNAs described above were prepared.

In other words, a 65-base DNA of, from the 5' terminal, CTGAGGTAG TCGCTACATTGGTAGGAATAGGATTG-CATGGGATACTATACACTGCACAGGCTTA C (SEQ ID NO: 5) was synthesized as a complementary DNA to be associated with the former DNA.

A 65-base DNA of, from the 5' terminal, GCACGTATAC-TAACTAAC TGTATTAGATCGGTAAGCCTGTGCAGT-GTATAGTATCCCATGCAATC (SEQ ID NO: 6) was synthesized as a complementary DNA to be associated with the latter DNA.

The structures of the synthesized thiol-terminated 33-base DNAs and the 65-base DNAs are as shown below.

```
DNA 1:
                                      (SEQ ID NO: 3)
5'-HS-C6-TTTCTATTCCTACCAATGTAGCGACTACCTCAG-C6-

TAMRA-3'

DNA 2:
                                      (SEQ ID NO: 4)
5'-HS-C6-TTTCGATCTAATACAGTTAGTTAGTATACGTGC-3'

DNA 3:
                                      (SEQ ID NO: 5)
5'-CTGAGGTAGTCGCTACATTGGTAGGAATAGGATTGCATGGGATACT

ATACACTGCACAGGCTTAC-3'

DNA 4:
                                      (SEQ ID NO: 6)
5'-GCACGTATACTAACTAACTGTATTAGATCGGTAAGCCTGTGCAGTGT

ATAGTATCCCATGCAATC-3'
```

<Production of Double-Stranded DNA>

These four samples of DNA were associated based on each complementary relationship to form a double-stranded structure. The method is not particularly limited but in this case, the following method was adopted.

In other words, each of the DNAs 1 to 4 was dissolved in pure water so as to independently give a concentration of 10 µM. After the dissolving, the DNAs were charged in a microtube at ratios of DNA 1:DNA 3=9:10 and DNA 2:DNA 4=9:10 by volume and were mixed. To the mixture, a 30 mM tris-hydroxymethylaminomethane-hydrochloric acid (pH 8) buffer containing 300 mM NaCl was added so that the final concentration of NaCl was adjusted to 100 mM. The sample tube was left at 90° C. for 10 minutes, and then was cooled to 30° C. at a cooling rate of −1° C./min. The associated DNAs were separated and purified by electrophoresis.

<Adsorption of DNA to Gold Particles (1): A Gold Nanoparticle Adsorbed with One DNA>

With 120 µL of gold nanoparticle dispersion liquid (manufactured by British BioCell International, Ltd.: particle size: 15 nm), 12 µL of previously-prepared anhydrous bis(p-sulfonatophenyl)phenylphosphine dipotassium salt solution (10 mg/mL aqueous solution, called BSPP) was mixed in a microtube, and gold nanoparticles having a surface coated with BSPP were formed. The mixed solution was centrifuged at 4° C. for 1 hour at 21,600 G, and then a supernatant liquid was discarded, resulting in a final volume of 10 µL.

The concentrated gold nanoparticle dispersion liquid was mixed with 2 µL tris-borate-EDTA (called TBE) buffer (0.5× TBE, containing 1.4 M NaCl).

To 4 µL of the solution, 2 µL of thiol-terminated DNA (2 µM) (DNA 1 or DNA 2 described above) was added and mixed. After the mixing, 0.5×TBE (containing 100 mM NaCl) was added to adjust the final volume to 8 µL and the mixed solution was left at room temperature (22° C.) for 24 hours. After leaving the mixture, 250 µL of BSPP (0.25 mg/mL solution) was mixed. The mixture was subjected to centrifugal sedimentation at 4° C. for 1 hour at 21,600 G, and then a supernatant liquid was discarded so that unreacted DNA was removed.

<Adsorption of DNA to Gold Particles (2): A Gold Nanoparticle Adsorbed with Two Samples of DNA>

In a similar manner to (1), 15-nm gold nanoparticles coated with BSPP were prepared. The purified DNA having the double-stranded structure synthesized in <Production of Double-Stranded DNA> described above was mixed at a molar ratio of (gold nanoparticle solution):(DNA solution)=5:1 in 0.5×TBE buffer (BSPP: 1 mg/mL, NaCl 166 mM). After the mixing, the mixture was left at room temperature for 24 hours, and the DNA was immobilized to the surface of the gold particle. Then, the immobilized DNA was left in a diluted BSPP solution (0.25 mg/mL solution) at 40° C., which dissociated the double strand. The product was purified by centrifuge purification (4° C., 1 hour, 21,600 G).

<Preparation of Gold Nanoparticle Aggregate>

Figure 12:
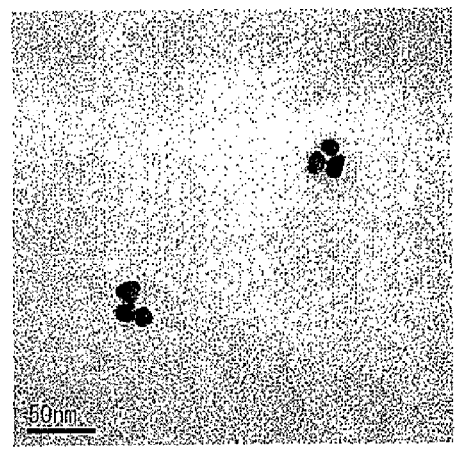
FIG. 12 is a view showing a transmission electron microscope image of gold nanoparticles obtained in Example 1, which are connected to each other and spaced apart a particular distance.

The DNA adsorbed gold nanoparticle dispersion liquids prepared in the adsorption of DNA to gold nanoparticles (1) and (2) (a: DNA 1 adsorbed gold nanoparticles, b: DNA 2 adsorbed gold nanoparticles, c: DNA 1 and DNA 2 adsorbed gold nanoparticles) were mixed at a volume ratio of a:b:c=1:1:10 and the mixture was left at room temperature for 24 hours. After leaving the mixture, the mixture was purified by centrifugation (−4° C., 10 minutes, 10,000 G) to remove gold nanoparticles that were not immobilized. A transmission electron microscope image of the obtained gold nanoparticle aggregate is shown in FIG. 12.

From the image, it was ascertained that three gold nanoparticles were bonded. In other words, by adding the c particles in an excess amount, an aggregate including a particle, c particle, and b particle which were bonded in a nonlinear fashion was obtained. The electric field formed on a particle interface of the gold nanoparticles thus obtained was substantially the same intensity as the result obtained in the test of Case 4 described above.

<Production of Molecular Recognition Probe-Containing Gold Nanoparticle Aggregate and Molecular Recognition>

With respect to the obtained gold nanoparticle aggregate solution, a hetero bifunctional PEG (a molecular weight of 5,000, 100 mM) having one terminal with an alkylamine and the other terminal with biotin was mixed at a ratio of 10% by mass as a molecular recognition probe molecule and the mixture was left at room temperature for 2 hours. Then, the mixture was purified by centrifugation to remove the unadsorbed sensing probe.

Figure 13:
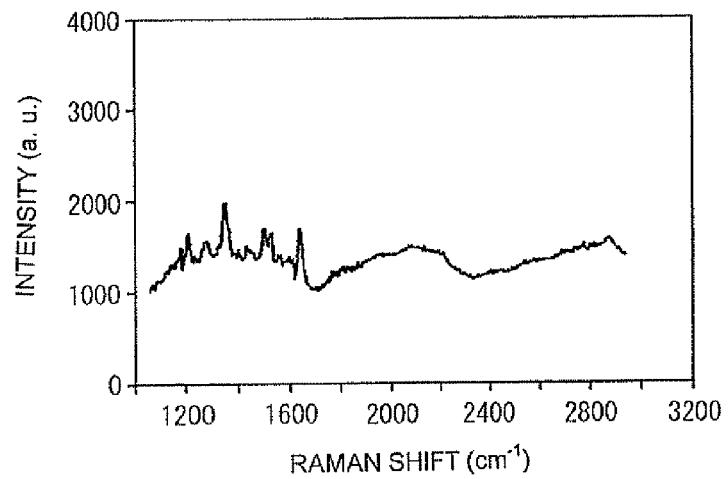
FIG. 13 is a view showing a molecular recognition result of streptavidin using the gold nanoparticles which are connected to each other and spaced apart a particular distance.

The molecular recognition probe-containing gold nanoparticle aggregate obtained in this manner was applied to a streptavidin plate. The plate was left at room temperature for several minutes, and then was washed with sterile water several times, thereby the molecular recognition probe-containing gold nanoparticles that were not immobilized were sufficiently washed until the plasmon absorption of gold disappeared from the washing water. The streptavidin plate treated in this manner was observed under a laser Raman microscope to afford a Raman scattering spectrum as shown in FIG. 13, and this revealed that the molecular recognition probe-containing gold nanoparticles could perform the molecular recognition.

Example 2

Three samples of DNA (DNAs 5, 6, 7, 8, 9, and 10) shown below were prepared.

```
DNA 5;
                                        (SEQ ID NO: 7)
5'-HS-TTTCTATTCCTACCAATGTAGCGACTACCTCAGTTTTTT-3'

DNA 6;
                                        (SEQ ID NO: 8)
5'-HS-TTTCGATCTAATACAGTTAGTTAGTATACGTGCTTTTTT-3'

DNA 7;
                                        (SEQ ID NO: 9)
5'-CTGAGGTAGTCGCTACATTGGTAGGAATAGGATTGCATGGGATAC-
3'

DNA 8;
                                        (SEQ ID NO: 10)
5'-GCACGTATACTAACTAACTGTATTAGATCGGTATCCCATGCAATC-
3'

DNA 9;
                                        (SEQ ID NO: 11)
5'-HS-TCTGAGGTAGTCGCTACATTGGTAGG-C6-TAMRA-3'

DNA 10;
                                        (SEQ ID NO: 12)
5'-HS-TGCACGTATACTAACTAACTGTATTA-C6-TAMRA-3'
```

In a similar manner to that shown in [Example 1], DNA 7 and DNA 8 were associated to form a DNA strand having a double strand at the center part (corresponding to DNA 3 having a double strand at the center part in FIG. 1) and then, with the single-stranded parts at both terminals of the DNA strand, DNA 5 and DNA 6 were associated to form double strands (corresponding to the modified DNA 4 in FIG. 1). The conditions for forming the double strands were entirely in accordance with Example 1.

To 1 mL of a gold nanoparticle solution, 5 nmol of the double-stranded DNA was added. After the addition, the container was stirred with a vortex mixer for 5 minutes, and then was left in a constant temperature chamber at 50° C. for 4 to 24 hours to accelerate the immobilization of the double-stranded DNA to the surface of a gold nanoparticle through a thiol group, which formed gold nanoparticles bonded with the DNA (corresponding to the gold nanoparticle 6 in FIG. 1). Next, the solution containing the gold nanoparticles was heated at 90° C. for 5 hours, and the double strand (corresponding to the gold nanoparticle 7 in FIG. 1) was dissociated.

Meanwhile, gold nanoparticles adsorbing DNA 9 and gold nanoparticles adsorbing DNA 10 (corresponding to the gold nanoparticle 8 and the gold nanoparticle 9 in FIG. 1) were independently prepared by the method described above in advance. The gold nanoparticles were added to the solution containing the gold nanoparticles, which afforded a gold nanoparticle aggregate (corresponding to the gold nanoparticle aggregate 10 in FIG. 1).

Figure 14:
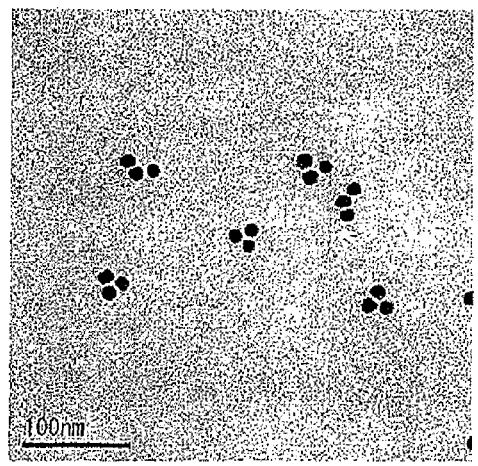
FIG. 14 is a view showing a transmission electron microscope image of gold nanoparticles obtained in Example 2, which are connected to each other and spaced apart a particular distance.

A transmission electron microscope image of the gold nanoparticle aggregate obtained is shown in FIG. 14. As shown in FIG. 14, three particles were bonded in a nonlinear fashion in the obtained aggregate.

[Case 7: Preparation of Nucleic Acid (DNA)]

TABLE 1

| DNA used | |
|---|---|
| DNA 11 (SEQ ID NO: 13) | DNA 12 (SEQ ID NO: 14) |
| Mw: 4,458 [g/mol] | Mw: 4,689 [g/mol] |
| Base number: 15 mer | Base number: 15 mer |
| Base sequence: TACGCCACCAGCTCC | Base sequence: GGAGCTGGTGGCGTA |
| OD (optical density): 5.5 | OD (optical density): 5.5 |

<Preparation and Purification of DNA>

First, a single-stranded DNA 11 and a single-stranded DNA 12 complementary to each other were prepared (see Table 1).

Subsequently, in each DNA 11 and DNA 12, a thiol group to be immobilized to a gold surface was bonded to the 5' terminal through a C6 linear alkyl group (C6).

Next, to the synthesized thiol-terminated DNA 11 (or DNA 12), DTT (dithiothreitol) was added in an amount of 200-fold volumes of the DNA, and the mixture was dissolved in a TE solution (tris-EDTA buffer: 10 mM tris-hydroxymethylaminomethane, 1 mM EDTA, a pH of less than 8). The solution was stirred with pipetting and a vortex, and then was reacted at ambient temperature for 2 hours. By the operation, the S—S bond that had been formed from some of DNA with an SH group was cleaved.

Then, to the DNA solution treated with DTT, 3 M aqueous sodium acetate solution was added in an amount of ¹⁄₁₀-fold volume of the DTT-treated DNA solution. Cold ethanol previously cooled at 4° C. was further added in an amount of 2.5-fold volume of the DNA solution. Then, the mixture was left in a freezer at −20° C. for 6 hours or more, which precipitated the DNA. The precipitated DNA was collected by centrifugation (4° C., 12,000 rpm; 7,740 G for 30 minutes). The purification by the ethanol precipitation and the centrifugation, that is, the cycle from the adding of 3 M aqueous sodium acetate solution to the precipitation and purification was further carried out twice.

[Case 8: Immobilization of Thiol-Terminated DNA to Gold Nanoparticles]

To 1 mL of gold nanoparticle dispersion liquid (manufactured by BBInternational: particle size: 10 nm), 5 nM of the thiol-terminated DNA (DNA 11 or DNA 12) in which the S—S bond had been reduced (cleaved) and that had been purified in Case 7 was added. The mixture was stirred with pipetting and a vortex for 1 minute, and then was left at 50° C. for 12 hours, which accelerated the immobilization of the DNA to the surface of a gold nanoparticle.

Figure 15:
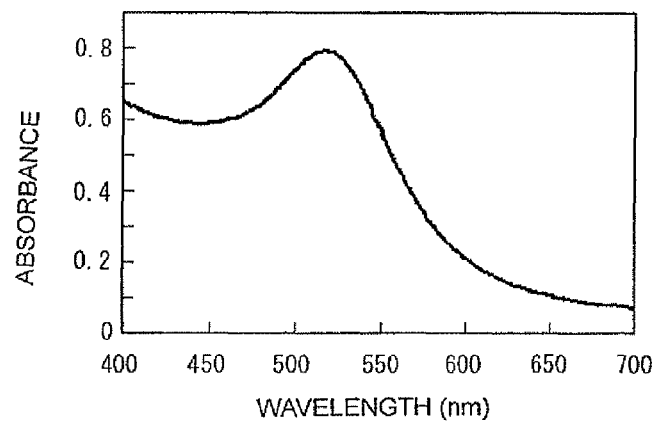
FIG. 15 is a view showing an ultraviolet-visible absorption spectrum of a dispersion liquid of gold nanoparticles adsorbing a thiol-terminated DNA 11 obtained in Case 8.

After leaving the mixture for 12 hours, the dispersion and aggregation state of the gold nanoparticles was observed by UV measurement. FIG. 15 shows an ultraviolet-visible absorption spectrum of the dispersion liquid of gold nanoparticles adsorbing the thiol-terminated DNA 11.

To each gold nanoparticle dispersion liquid, 40 μL of 2.5 M NaCl and 20 μL of 500 mM phosphate buffer (pH 7) were added and the mixture was further left at 50° C. for 40 hours.

By the operation, NaCl took negative (−) charges on the gold surface, and the thiol-terminated DNA that had not been adsorbed onto the surface of the gold nanoparticle and that remained in the solution, was further adsorbed onto the surface of the gold nanoparticle.

Figure 16:
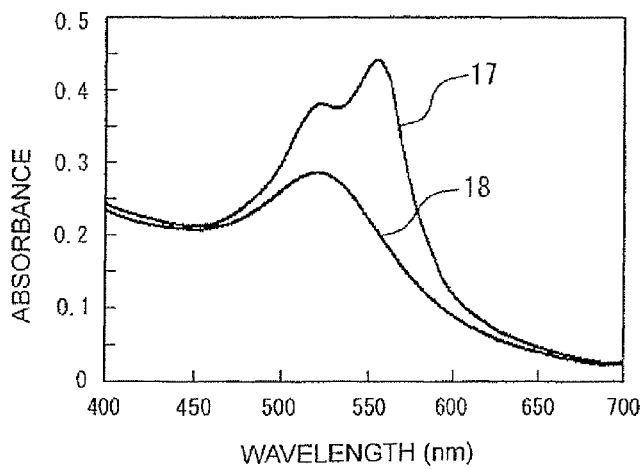
FIG. 16 is a view showing ultraviolet-visible absorption spectra of dispersion liquids of gold nanoparticles further adsorbing a thiol-terminated DNA 11 or a thiol-terminated DNA 12 obtained in Case 8 (DNA 11: sign 17, DNA 12: sign 18).

After leaving the mixture for 40 hours, the dispersion and aggregation state of the gold nanoparticles was observed by UV measurement. FIG. 16 shows ultraviolet-visible absorption spectra of the dispersion liquids of gold nanoparticles adsorbing the thiol-terminated DNA 11 (the sign 17 in FIG. 16) and the thiol-terminated DNA 12 (the sign 18 in FIG. 16).

[Case 9: Production of Gold Nanoparticle Aggregate]

Each of the solution of gold nanoparticles immobilized with DNA 11 by the above procedure and the solution of gold nanoparticles immobilized with DNA 12 complementary to the DNA 11, by the above procedure, was centrifuged at 13,000 rpm for 30 minutes to precipitate the gold nanoparticles, and the supernatant liquid was removed. To the residue, 0.5 mL of 10 mM phosphate buffer (containing 0.1 M NaCl, pH 7) was added and the precipitate was redispersed. The dispersion liquid was centrifuged once again at 13,000 rpm for 30 minutes, then the supernatant liquid was removed, and the residue was redispersed in 1 µL of 0.01% tween-20 and 0.25 mL of 10 mM phosphate buffer (containing 0.1 M NaCl, pH 7).

Figure 17:
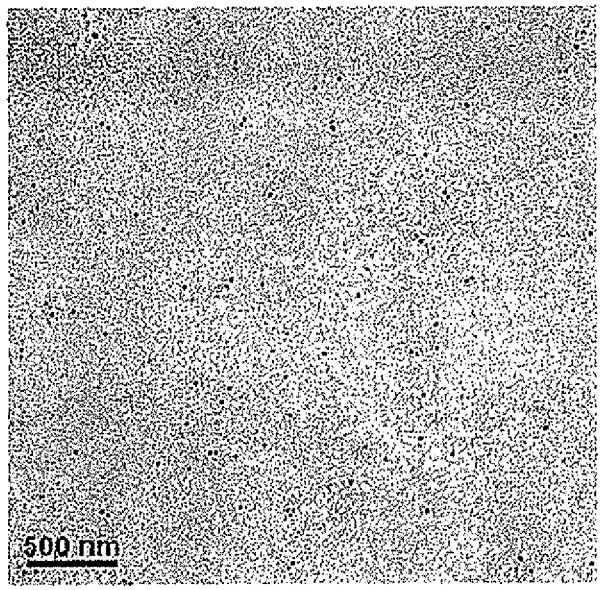
FIG. 17 is a view showing a transmission electron microscope image of a sample [1] solution obtained in Case 9.
Figure 18:
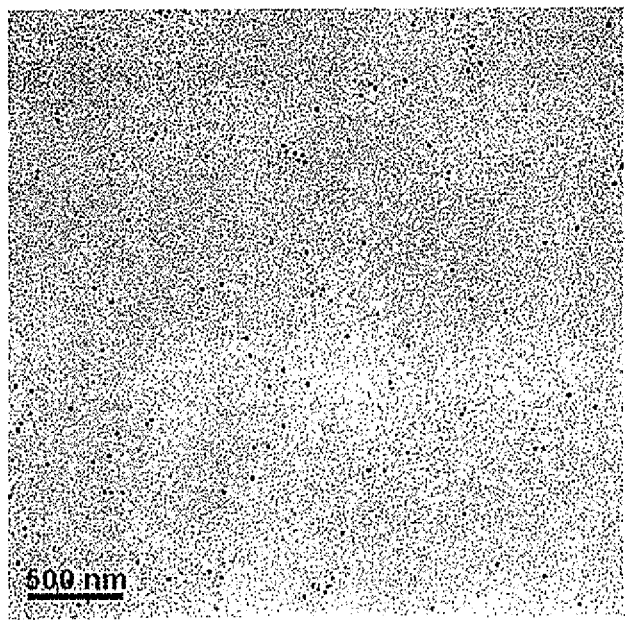
FIG. 18 is a view showing a transmission electron microscope image of a sample [2] solution obtained in Case 9.

The gold nanoparticle dispersion liquid prepared using the DNA 11 was regarded as a sample [1] solution, while the gold nanoparticle dispersion liquid prepared using the DNA 12 was regarded as a sample [2] solution. The observed results of the sample solutions under a transmission electron microscope are shown in FIG. 17 and FIG. 18.

Two dispersion solutions of gold nanoparticles that had surfaces bonded with DNAs and were obtained in this manner were mixed and the complementary strands of the DNAs were associated. As a result, a bond between the gold nanoparticles was formed, which produced a gold nanoparticle aggregate.

That is, first, into a 1.5-mL microtube, 1 µL of 1% tween-20, 10 µL of sample [1] solution, 10 µL of sample [2] solution, and 4 µL of 5 M NaCl were added, and the mixture was left in a high temperature chamber at 75° C. for 1 hour, and then was left standing at room temperature for 10 minutes.

After leaving the mixture for 10 minutes, it was ascertained that the solution color changed from red to violet and the mixture was further left standing for 20 minutes. Then, the mixture was lightly centrifuged, and the obtained aggregate was precipitated.

Figure 19:
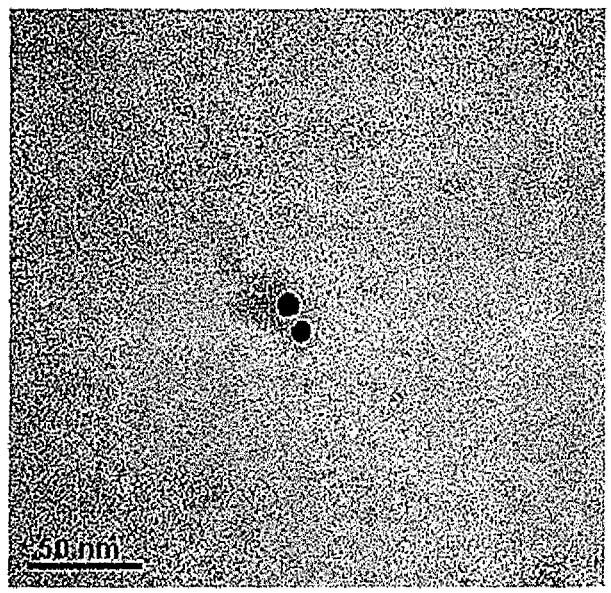
FIG. 19 is a view showing a transmission electron microscope image of a gold nanoparticle aggregate obtained in Case 9.

A transmission electron microscope (TEM) image of the obtained gold nanoparticle aggregate is shown in FIG. 19.

[Case 10: Modification of Gold Particle Surface with DNAs Having Various Base Numbers]

<Preparation of DNA>

Each of the three samples of DNA (DNA 13 to DNA 15) shown in Table 2 was treated as follows.

To the thiol-terminated DNA (DNA 13 to DNA 15), DTT (dithiothreitol) was added in an amount of 200-fold volume of the DNA and the mixture was dissolved in a TE solution (tris-EDTA buffer: 10 mM tris-hydroxymethylaminomethane, 1 mM EDTA, a pH of less than 8). The solution was stirred with pipetting and a vortex, and then was reacted at ambient temperature for 2 hours.

Then, to the DNA solution treated with DTT, 3 M aqueous sodium acetate solution was added in an amount of ¹⁄₁₀-fold volume of the DTT-treated DNA solution. To the DNA solution, cold ethanol previously cooled at 4° C. was further added in an amount of 2.5-fold volume of the DNA solution. Then, the mixture was left in a freezer at −20° C. for 6 hours or more, which precipitated the DNA. The precipitated DNA was collected by centrifugation (4° C., 12,000 rpm; 7,740 G for 30 minutes). The purification by the ethanol precipitation and the centrifugation, that is, the cycle from the adding of 3 M aqueous sodium acetate solution to the precipitation and purification was further carried out twice.

TABLE 2

| | Three samples of DNA used in experiment | | |
|---|---|---|---|
| Name | DNA 13 (SEQ ID NO: 15) | DNA 14 (SEQ ID NO: 16) | DNA 15 (SEQ ID NO: 17) |
| Picomole | 12,558 | 19,220 | 29,940 |
| Mw [g/mol] | 12,676 | 8,113 | 4,689 |
| Base number [mer] | 42 | 27 | 15 |
| Tm | 75.2 | 71.7 | 50.0 |
| Base sequence | XTT TTT TTT TTT TTT TTT TTT TTT TTT TAC GCC ACC AGC TCC | XTT TTT TTT TTT TAC GCC ACC AGC TCC | GCC GCT GGT GGC GTA |
| OD | 5.00 | 5.00 | 5.00 |

X: TAMRA-dt

<Immobilization of Thiol-Terminated DNA to Gold Nanoparticles>

To 1 mL of gold nanoparticle dispersion liquid (manufactured by BBInternational: particle size: 10 nm), 5 nM of the thiol-terminated DNA purified by the process described above (DNA 13 to DNA 15) was added. The mixture was stirred with pipetting and a vortex for 1 minute, and then was left at 50° C. for 24 hours, which accelerated the immobilization of the DNA to the surface of a gold nanoparticle.

Figure 20:
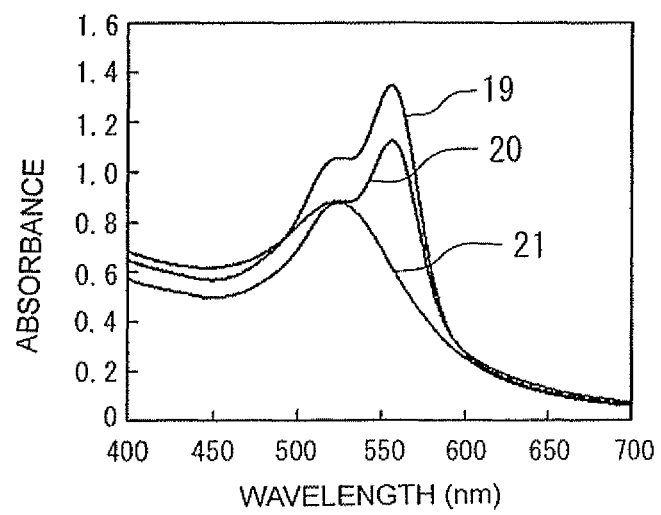
FIG. 20 is a view showing ultraviolet-visible absorption spectra of dispersion liquids of gold nanoparticles adsorbing a thiol-terminated DNA 13, a thiol-terminal 14, or a thiol-terminal 15 obtained in Case 10 (DNA 13: sign 19, DNA 14: sign 20, DNA 15: sign 21).

After leaving the mixture for 12 hours, to each gold nanoparticle dispersion liquid, 40 µL of 2.5 M NaCl and 50 µL of 200 mM phosphate buffer (pH 7) were added and the mixture was further left at 50° C. for 45 hours. FIG. 20 shows ultraviolet-visible absorption spectra of gold nanoparticle dispersion liquids adsorbing respective thiol-terminated DNAs (in the figure, DNA 13: sign 19, DNA 14: sign 20, DNA 15: sign 21) after leaving the liquids.

Each of the three solutions of gold nanoparticles immobilized with respective three samples of DNA (DNA 13 to DNA 15) was then centrifuged at 14,000 rpm (18,700 G) for 30 minutes, the gold nanoparticles were precipitated, and the supernatant liquid was removed. To the residue, 0.5 mL of 10 mM phosphate buffer (containing 0.1 M NaCl, pH 7) was added and the precipitate was redispersed. The dispersion liquid was centrifuged once again at 14,000 rpm for 30 minutes, then the supernatant liquid was removed, and the residue was redispersed in 1 μL of 0.01% tween-20 and 0.25 mL of 10 mM phosphate buffer (containing 0.1 M NaCl, pH 7).

The gold nanoparticles prepared using DNA 13 was regarded as a sample [3] solution, the gold nanoparticles prepared using DNA 14 was regarded as a sample [4] solution, and the gold nanoparticles prepared using DNA 15 was regarded as a sample [5] solution. FIG. 21 shows each ultraviolet-visible absorption spectrum of the sample solutions (in the figure, DNA 13: sign 19, DNA 14: sign 20, DNA 15: sign 21).

<Production of Gold Nanoparticle Aggregate (1): Sample [3] Solution and Sample [5] Solution>

Into a 1.5-mL microtube, 1 μL of 1% tween-20, 10 μL of sample [3] solution (DNA strand length: 42 mer), 10 μL of sample [5] solution (DNA strand length: 15 mer), and 4 μL of 5 M NaCl were charged. The mixture was left in a high temperature chamber at 75° C. for 1 hour, and then was left standing at room temperature for 10 minutes.

After leaving the mixture for 10 minutes, it was ascertained that the solution color changed from red to violet, and the mixture was further left standing for 20 minutes. Then, the mixture was lightly centrifuged and the complementary strands of the DNAs were associated. As a result, a bond between the gold nanoparticles was formed, which produced a gold nanoparticle aggregate. The obtained aggregate is regarded as a sample [6].

<Production of Gold Nanoparticle Aggregate (2): Sample 141 Solution and Sample [5] Solution>

Into a 1.5-mL microtube, 1 μL of 1% tween-20, 10 μL of sample [4] solution (DNA strand length: 27 mer), 10 μL of sample [5] solution (DNA strand length: 15 mer), and 4 μL of 5 M NaCl were charged. The mixture was left in a high temperature chamber at 75° C. for 1 hour, and then was left standing at room temperature for 10 minutes.

After leaving the mixture for 10 minutes, it was ascertained that the solution color changed from red to violet, and the mixture was further left standing for 20 minutes. Then, the mixture was slightly centrifuged and the complementary strands of the DNAs were associated. As a result, a bond between the gold nanoparticles was formed, which produced a gold nanoparticle aggregate. The obtained aggregate is regarded as a sample [7].

The appearances (photographs) of the obtained sample [6] and sample [7] are shown in FIG. 22.

Example 3

Molecular Recognition by Nucleic Acid

A molecule in which a terminal of aptamer AS1411 that is one of the nucleic acid preparations against lung cancer was modified with a thiol group (purchased from Tsukuba Oligo Service Co., Ltd.) was adsorbed onto the surface of the gold nanoparticle aggregate produced in Case 9 and the product was applied to lung cancer cells (a549). The Raman scattering spectra before and after the application were compared.

In particular, to a dispersion liquid of the gold nanoparticle aggregate produced in accordance with Case 9 (dispersed in 10 mM phosphate buffer (pH 7.0)), 5 nM aptamer AS1411 solution was added and the mixture was stirred at 40° C. for 24 hours. Then, the mixture was centrifuged at 14,000 rpm (18,700 G) for 30 minutes, the particles were precipitated, and the supernatant liquid was removed. To the residue, 0.5 mL of 10 mM phosphate buffer (containing 0.1 M NaCl, pH 7) was added and the precipitate was redispersed. The dispersion liquid was centrifuged once again at 14,000 rpm for 30 minutes, then the supernatant liquid was removed, and the residue was redispersed in 1 μL of 0.01% tween-20 and 0.25 mL of 10 mM phosphate buffer (containing 0.1 M NaCl, pH 7).

To lung cancer cells cultured in a culture dish in advance, 20 uL of the AS1411-adsorbed gold nanoparticle aggregate obtained as above was added. The whole was left for 48 hours so that the gold nanoparticle aggregate was adsorbed to the cancer cells. Then, the cancer cell surface was observed with a Raman spectrometer and the Raman scattering spectrum of the cancer cell surface before the adsorption was compared with that of the cancer cell surface after the adsorption. FIG. 23 shows a Raman scattering spectrum of the AS1411-adsorbed gold nanoparticle aggregate, FIG. 24 shows a Raman scattering spectrum of the a549 cancer cells, and FIG. 25 shows a Raman scattering spectrum of the a549 cancer cells adsorbing the AS1411-adsorbed gold nanoparticle aggregate.

Figure 24:
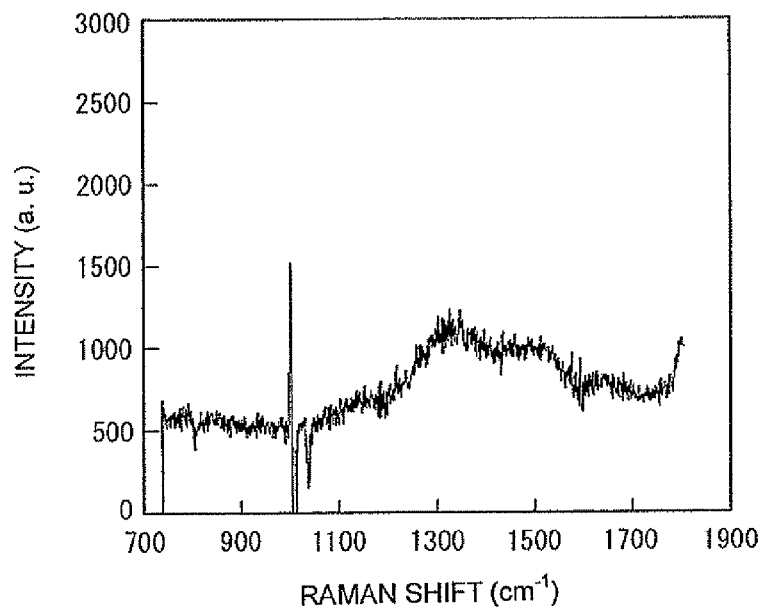
FIG. 24 is a view showing the result of resonance Raman scattering measurement of a549 cancer cells.
Figure 25:
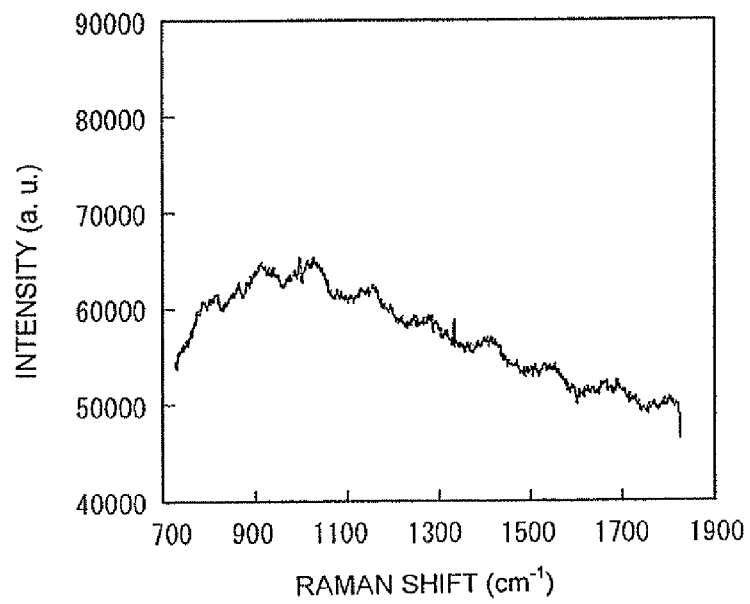
FIG. 25 is a view showing the result of resonance Raman scattering measurement of a549 cancer cells adsorbing the AS1411-adsorbed gold nanoparticle aggregate.

As shown in FIG. 24 to FIG. 25, by applying the AS1411-adsorbed gold nanoparticle aggregate to the cancer cells, the Raman scattering spectrum largely changed and this ascertained that the gold nanoparticle aggregate produced in Case 9 can perform the molecular recognition.

Example 4

Molecular Recognition by Nucleic Acid

A molecule in which a terminal of aptamer AS1411 that is one of the nucleic acid preparations against lung cancer was modified with a thiol group (purchased from Tsukuba Oligo Service Co., Ltd.) was adsorbed onto the surface of the gold nanoparticle aggregate produced by the method described in Example 3 and the product was applied to lung cancer cells (a549), and the mapping of adsorption sites was performed.

To lung cancer cells cultured in a culture dish in advance, 20 uL of the AS1411-adsorbed gold nanoparticle aggregate obtained was added. The whole was left for 48 hours so that the gold nanoparticle aggregate was adsorbed to the cancer cells. Then, the cancer cell surface was observed with a Raman spectrometer. The Raman spectrum relating to the adsorption was analyzed for the mapping derived from phosphoric acid of DNA derived from the cancer cells, the mapping of the gold particle adsorption part, and the overlapping comparison of micrographs. As a result, it was ascertained that the cancer cells could be recognized.

INDUSTRIAL APPLICABILITY

The metal nanoparticle material for molecular sensing of the present invention is useful as a high-sensitive molecular recognition sensor and can be used as a suitable material for recognition of trace amount of molecules, that is, for sensing of biological substances.

DESCRIPTION OF THE REFERENCE NUMERALS

1. Thiol-terminated single-stranded DNA 1
2. Single-stranded DNA 2 complementary to DNA 1
3. DNA 3 having the center part with a double-stranded DNA and both terminals with single-stranded DNAs 1 and 2

4. DNA 4 in which DNA 1 and DNA 2 are associated with both terminals of DNA 3
5. Gold nanoparticle
6. Gold nanoparticle having a surface bonded with DNA 4 through thiol groups
7. Separated gold nanoparticle after dissociating the double strand by heating
8. Gold nanoparticle adsorbing a single-stranded DNA 1
9. Gold nanoparticle adsorbing a complementary strand DNA 2
10. Gold nanoparticle aggregate
11. Position information of a gold nanoparticle bonded with a single-stranded DNA (b)
12. Electric field information coming from the gold nanoparticle bonded with the single-stranded DNA (b)
13. Position information of gold nanoparticles in a gold nanoparticle aggregate
14. Electric field information coming from the gold nanoparticles in the gold nanoparticle aggregate
15. Enhanced Raman scattering of gold nanoparticles in an adjacent state in a gold nanoparticle aggregate
16. Enhanced Raman scattering of gold nanoparticles after the gold nanoparticle aggregate was dissociated by heating
17. Ultraviolet-visible absorption spectrum of a dispersion liquid of gold nanoparticles adsorbing the thiol-terminated DNA 11
18. Ultraviolet-visible absorption spectrum of a dispersion liquid of gold nanoparticles adsorbing the thiol-terminated DNA 12
19. Ultraviolet-visible absorption spectrum of a dispersion liquid of gold nanoparticles adsorbing the thiol-terminated DNA 13
20. Ultraviolet-visible absorption spectrum of a dispersion liquid of gold nanoparticles adsorbing the thiol-terminated DNA 14
21. Ultraviolet-visible absorption spectrum of a dispersion liquid of gold nanoparticles adsorbing the thiol-terminated DNA 15

The invention claimed is:

1. A method for producing a metal nanoparticle material for molecular sensing, the method comprising:
   a) associating a single-stranded nucleic acid strand as a substrate with at least two single-stranded nucleic acid strands each having complementarity to a partial base structure in the nucleic acid strand and having one terminal with a thiol group to form a double helix, thereby obtaining a modified nucleic acid strand;
   b) reacting the thiol groups in the modified nucleic acid strand with a metal nanoparticle to bond the modified nucleic acid strand onto the surface of the metal nanoparticle, and then heating the resulting product at 60 to 100° C. to dissociate the double helix structure of the modified nucleic acid strand, thereby removing the single-stranded nucleic acid strand to obtain a metal nanoparticle bonded with the single-stranded nucleic acid strands through the thiol groups;
   c) reacting a single-stranded nucleic acid strand having complementarity to the nucleic acid strands, having one terminal with a thiol group, and having a base length equal to that of the nucleic acid strands with a metal nanoparticle, thereby obtaining a metal nanoparticle bonded with the single-stranded nucleic acid strand through the thiol group;
   d) mixing the metal nanoparticle bonded with the single-stranded nucleic acid strands and the metal nanoparticle bonded with the single-stranded nucleic acid strand to associate the single-stranded nucleic acid strands with the single-stranded nucleic acid strand, thereby forming a double helix to produce a metal nanoparticle aggregate; and
   bonding a Raman active molecule to:
      the single-stranded nucleic acid strands used in a);
      the single-stranded nucleic acid strand used in c); or
      the single-stranded nucleic acid strands used in a) and the single-stranded nucleic acid strand used in c);
   wherein:
   the metal nanoparticle material comprises a metal nanoparticle aggregate including three to ten metal nanoparticles connected to each other through an organic molecule so that adjacent metal nanoparticles are bonded and spaced apart a predetermined distance, the aggregate containing a Raman active molecule within a field applied to the aggregate; and
   the metal nanoparticle material emits enhanced Raman scattering light from the Raman active molecule in an enhanced electric field.

2. A method for producing a metal nanoparticle material for molecular sensing, the method comprising:
   a) associating a single-stranded DNA strand as a substrate with at least two single-stranded DNA strands each having complementarity to a partial base structure in the DNA strand and having one terminal with a thiol group to form a double helix, thereby obtaining a modified DNA strand;
   b) reacting the thiol groups in the modified DNA strand with a metal nanoparticle to bond the modified DNA strand onto the surface of the metal nanoparticle, and then heating the resulting product at 60 to 100° C. to dissociate the double helix structure of the modified DNA strand, thereby removing the single-stranded DNA strand to obtain a metal nanoparticle bonded with the single-stranded DNA strands through the thiol groups;
   c) reacting a single-stranded DNA strand having complementarity to the DNA strands, having one terminal with a thiol group, and having a base length equal to that of the DNA strands with a metal nanoparticle, thereby obtaining a metal nanoparticle bonded with the single-stranded DNA strand through the thiol group;
   d) mixing the metal nanoparticle bonded with the single-stranded DNA strands and the metal nanoparticle bonded with the single-stranded DNA strand to associate the single-stranded DNA strands with the single-stranded DNA strand, thereby forming a double helix to produce a metal nanoparticle aggregate; and
   bonding a Raman active molecule to:
      the single-stranded DNA strands used in a);
      the single-stranded DNA strand used in c); or
      the single-stranded DNA nucleic acid strands used in a) and the single-stranded DNA nucleic acid strand used in c);
   wherein:
   the metal nanoparticle material comprises a metal nanoparticle aggregate including three to ten metal nanoparticles connected to each other through an organic molecule so that adjacent metal nanoparticles are bonded and spaced apart a predetermined distance, the aggregate containing a Raman active molecule within a field applied to the aggregate; and
   the metal nanoparticle material emits enhanced Raman scattering light from the Raman active molecule in an enhanced electric field.

3. The method for producing the metal nanoparticle material for molecular sensing according to claim 2, wherein in d), 2 equivalents of the metal nanoparticle bonded with the single-stranded DNA strand is used with respect to 1 equivalent of the metal nanoparticle bonded with the single-stranded DNA strands to produce the metal nanoparticle aggregate.

4. The method for producing the metal nanoparticle material for molecular sensing according to claim 2, wherein the single-stranded DNA strands do not have a part complementary to each other.

5. The method for producing the metal nanoparticle material for molecular sensing according to claim 2, further comprising, in any of a) to d):
   e) reacting the metal nanoparticles with a molecular recognition probe molecule which includes a molecular chain containing a nucleic acid, polyethylene glycol, or a hydrocarbon, the molecular chain having one terminal with a molecular recognition probe and having another terminal with a thiol group or an amino group, thereby bonding the molecular recognition probe molecule at the terminal to the surfaces of the metal nanoparticles through the thiol group or the amino group.

6. A molecular sensing method comprising:
   bringing the metal nanoparticle material for molecular sensing produced according to claim 1 into contact with a specimen, and then performing Raman scattering measurement of the specimen.

7. The molecular sensing method according to claim 6, wherein the metal nanoparticle material for molecular sensing is immobilized onto a substrate.

* * * * *

```
                         SEQUENCE LISTING

<160> NUMBER OF SEQ ID NOS: 17

<210> SEQ ID NO 1
<211> LENGTH: 12
<212> TYPE: DNA
<213> ORGANISM: Artificial Sequence
<220> FEATURE:
<223> OTHER INFORMATION: Synthetic Construct

<400> SEQUENCE: 1
gccaccagct cc                                                             12

<210> SEQ ID NO 2
<211> LENGTH: 12
<212> TYPE: DNA
<213> ORGANISM: Artificial Sequence
<220> FEATURE:
<223> OTHER INFORMATION: Synthetic Construct

<400> SEQUENCE: 2
ggagctggtg gc                                                             12

<210> SEQ ID NO 3
<211> LENGTH: 33
<212> TYPE: DNA
<213> ORGANISM: Artificial Sequence
<220> FEATURE:
<223> OTHER INFORMATION: Synthetic Construct

<400> SEQUENCE: 3
tttctattcc taccaatgta gcgactacct cag                                      33

<210> SEQ ID NO 4
<211> LENGTH: 33
<212> TYPE: DNA
<213> ORGANISM: Artificial Sequence
<220> FEATURE:
<223> OTHER INFORMATION: Synthetic Construct

<400> SEQUENCE: 4
tttcgatcta atacagttag ttagtatacg tgc                                      33

<210> SEQ ID NO 5
<211> LENGTH: 65
<212> TYPE: DNA
```

<213> ORGANISM: Artificial Sequence
<220> FEATURE:
<223> OTHER INFORMATION: Synthetic Construct

<400> SEQUENCE: 5
ctgaggtagt cgctacattg gtaggaatag gattgcatgg gatactatac actgcacagg    60
cttac    65

<210> SEQ ID NO 6
<211> LENGTH: 65
<212> TYPE: DNA
<213> ORGANISM: Artificial Sequence
<220> FEATURE:
<223> OTHER INFORMATION: Synthetic Construct

<400> SEQUENCE: 6
gcacgtatac taactaactg tattagatcg gtaagcctgt gcagtgtata gtatcccatg    60
caatc    65

<210> SEQ ID NO 7
<211> LENGTH: 39
<212> TYPE: DNA
<213> ORGANISM: Artificial Sequence
<220> FEATURE:
<223> OTHER INFORMATION: Synthetic Construct

<400> SEQUENCE: 7
tttctattcc taccaatgta gcgactacct cagttttt    39

<210> SEQ ID NO 8
<211> LENGTH: 39
<212> TYPE: DNA
<213> ORGANISM: Artificial Sequence
<220> FEATURE:
<223> OTHER INFORMATION: Synthetic Construct

<400> SEQUENCE: 8
tttcgatcta atacagttag ttagtatacg tgctttttt    39

<210> SEQ ID NO 9
<211> LENGTH: 45
<212> TYPE: DNA
<213> ORGANISM: Artificial Sequence
<220> FEATURE:
<223> OTHER INFORMATION: Synthetic Construct

<400> SEQUENCE: 9
ctgaggtagt cgctacattg gtaggaatag gattgcatgg gatac    45

<210> SEQ ID NO 10
<211> LENGTH: 45
<212> TYPE: DNA
<213> ORGANISM: Artificial Sequence
<220> FEATURE:
<223> OTHER INFORMATION: Synthetic Construct

<400> SEQUENCE: 10
gcacgtatac taactaactg tattagatcg gtatcccatg caatc    45

<210> SEQ ID NO 11
<211> LENGTH: 26
<212> TYPE: DNA
<213> ORGANISM: Artificial Sequence
<220> FEATURE:
<223> OTHER INFORMATION: Synthetic Construct

```
<400> SEQUENCE: 11
tctgaggtag tcgctacatt ggtagg                                          26

<210> SEQ ID NO 12
<211> LENGTH: 26
<212> TYPE: DNA
<213> ORGANISM: Artificial Sequence
<220> FEATURE:
<223> OTHER INFORMATION: Synthetic Construct

<400> SEQUENCE: 12
tgcacgtata ctaactaact gtatta                                          26

<210> SEQ ID NO 13
<211> LENGTH: 15
<212> TYPE: DNA
<213> ORGANISM: Artificial Sequence
<220> FEATURE:
<223> OTHER INFORMATION: Synthetic Construct

<400> SEQUENCE: 13
tacgccacca gctcc                                                      15

<210> SEQ ID NO 14
<211> LENGTH: 15
<212> TYPE: DNA
<213> ORGANISM: Artificial Sequence
<220> FEATURE:
<223> OTHER INFORMATION: Synthetic Construct

<400> SEQUENCE: 14
ggagctggtg gcgta                                                      15

<210> SEQ ID NO 15
<211> LENGTH: 41
<212> TYPE: DNA
<213> ORGANISM: Artificial Sequence
<220> FEATURE:
<223> OTHER INFORMATION: Synthetic Construct

<400> SEQUENCE: 15
tttttttttt tttttttttt tttttttacg ccaccagctc c                         41

<210> SEQ ID NO 16
<211> LENGTH: 26
<212> TYPE: DNA
<213> ORGANISM: Artificial Sequence
<220> FEATURE:
<223> OTHER INFORMATION: Synthetic Construct

<400> SEQUENCE: 16
tttttttttt ttacgccacc agctcc                                          26

<210> SEQ ID NO 17
<211> LENGTH: 15
<212> TYPE: DNA
<213> ORGANISM: Artificial Sequence
<220> FEATURE:
<223> OTHER INFORMATION: Synthetic Construct

<400> SEQUENCE: 17
gccgctggtg gcgta                                                      15
```